(12) United States Patent
Hara et al.

(10) Patent No.: US 9,108,431 B2
(45) Date of Patent: Aug. 18, 2015

(54) PRINTER AND TABLET

(71) Applicants: Otsuka Pharmaceutical Co., Ltd., Tokyo (JP); OKABE Industrial Machineries CO., LTD., Anan-shi (JP)

(72) Inventors: Yoshio Hara, Osaka (JP); Takeshi Matsuda, Osaka (JP); Tadashi Mukai, Osaka (JP); Toshiyuki Hoshiba, Anan (JP); Keiji Kimoto, Anan (JP); Hiromichi Makino, Anan (JP)

(73) Assignees: Otsuka Pharmaceuticals Co., Ltd., Tokyo (JP); OKABE Industrial Machineries CO., LTD., Anan-shi (JP)

( * ) Notice: Subject to any disclaimer, the term of this patent is extended or adjusted under 35 U.S.C. 154(b) by 0 days.

(21) Appl. No.: 14/415,464

(22) PCT Filed: Jul. 16, 2013

(86) PCT No.: PCT/JP2013/069263
§ 371 (c)(1),
(2) Date: Jan. 16, 2015

(87) PCT Pub. No.: WO2014/013974
PCT Pub. Date: Jan. 23, 2014

(65) Prior Publication Data
US 2015/0174916 A1 Jun. 25, 2015

(30) Foreign Application Priority Data
Jul. 19, 2012 (JP) ................................. 2012-160720
Jul. 19, 2012 (JP) ................................. 2012-160729

(51) Int. Cl.
*B41J 2/00* (2006.01)
*B41J 3/407* (2006.01)
*B41J 11/06* (2006.01)

(52) U.S. Cl.
CPC . *B41J 3/407* (2013.01); *B41J 11/06* (2013.01)

(58) Field of Classification Search
None
See application file for complete search history.

(56) References Cited

U.S. PATENT DOCUMENTS 4,189,996 A * 2/1980 Ackley et al. .................. 101/37
2012/0132722 A1 5/2012 Ackley, Jr. et al.

FOREIGN PATENT DOCUMENTS

| JP | 07081050 A | 3/1995 |
| JP | 09110142 A | 4/1997 |
| JP | 09187915 A | 7/1997 |
| JP | 2005125000 A | 5/2005 |

* cited by examiner

*Primary Examiner* — Geoffrey Mruk
*Assistant Examiner* — Bradley Thies
(74) *Attorney, Agent, or Firm* — The Webb Law Firm

(57) ABSTRACT

A printer of the present invention includes a first printing device capable of performing printing on a face facing one side in an orthogonal direction to a conveyance direction of a tablet while being conveyed and a second printing device capable of performing printing on a face facing the other side in the orthogonal direction of the tablet while being conveyed.

3 Claims, 25 Drawing Sheets

PRINTER AND TABLET

CROSS-REFERENCE TO RELATED APPLICATIONS

This application is the United States national phase of International Application No. PCT/JP2013/069263 filed Jul. 16, 2013, and claims priority to Japanese Patent Application Nos. 2012-160729 and 2012-160720, filed Jul. 19, 2012, the disclosures of which are hereby incorporated in their entirety by reference.

BACKGROUND OF THE INVENTION

1. Field of the Invention

The present invention relates to a printer performing printing on a tablet. Further, the present invention relates to a tablet that is manufactured using the printer.

2. Background Art

Conventionally, printers have been known which perform printing on an object such as a tablet and a candy. Such a printer includes a conveying device which conveys an object and a printing device which performs printing on one face of the object to be conveyed (for example, Patent Literature 1). With such a printer, the printing device performs printing on one face of the object, and thus, printing is continuously performed on a plurality of objects while being conveyed.

However, the printer according to Patent Literature 1 can perform printing on only one face of the conveyed object, and can perform neither printing on the both faces of the object while being conveyed nor perform printing on a desired one out of a face facing one side and a face facing the other side of the object while being conveyed.

CITATION LIST

Patent Literature

Patent Literature 1: JP-A-7-81050

SUMMARY OF THE INVENTION

Problems to be Solved by the Invention

Therefore, the present invention has been made in view of these circumstances, and an object of the present invention is to provide a printer which can perform printing on both faces of the tablet while being conveyed or can perform printing on a desired one out of a face facing one side and a face facing the other side of the tablet while being conveyed.

Further, another object of the present invention is to provide a tablet on which printing is performed on at least one face out of one side and the other side.

Means for Solving Problems

The printer according to the present invention includes a conveying device that conveys a tablet, a first printing device capable of performing printing on a face facing one side in an orthogonal direction to a conveyance direction of a tablet while being conveyed, and a second printing device capable of performing printing on a face facing the other side in the orthogonal direction of the tablet while being conveyed.

According to this configuration, the conveying device conveys a tablet. The first printing device can perform printing on the face facing the one side in the orthogonal direction of the tablet while being conveyed, and the second printing device can perform printing on the face facing the other side in the orthogonal direction of the tablet while being conveyed. Whereby, the printer can perform printing on the both faces of the tablet while being conveyed, or can perform printing on a desired one face out of the face facing the one side and the face facing the other side of the tablet while being conveyed.

There is a case where the tablet has a groove-shaped dividing line for dividing the tablet on at least one face out of the face facing the one side and the face facing the other side. In this case, it is preferable that the first printing device and the second printing device perform printing at a position excluding (while avoiding printing on) the dividing line.

According to the above-described configuration, a symbol, or the like, is printed while a dividing line or a portion corresponding to the dividing line of the tablet is excluded from a portion on which printing is to be performed. Whereby, it is possible to prevent the printed symbol, or the like, from being divided when the tablet is divided along the dividing line.

Further, the printer includes an aligning section that supplies a plurality of tablets to the conveying device in a state where the plurality of tablets are aligned in the conveyance direction. In this case, the conveying device preferably has a dividing line direction aligning section that is disposed at an upstream side of the first printing device and the second printing device and that aligns a direction of the dividing line of each tablet in a predetermined direction.

According to the above-described configuration, a plurality of tablets are supplied to printing positions of the printing devices (the first printing device and the second printing device) in such a manner that the dividing lines of the tablets are aligned in a given direction (predetermined direction) and the tablets are aligned in the conveyance direction. Therefore, it is possible to facilitate continuous printing of symbols, or the like, at predetermined positions relative to the dividing lines on the plurality of tablets.

The dividing line direction aligning section may have a protrusion which extends in the conveyance direction and which has a cross-sectional shape corresponding to a cross-sectional shape of the dividing line of the tablet and a contact body which rotates the tablet around the predetermined axis facing in the orthogonal direction, the tablet being placed on the protrusion such that, out of the face facing the one side and the face facing the other side, a face on which the dividing line is provided contacts the protrusion, and a direction of the dividing line is different from a direction of the protrusion.

By rotating the tablet which is placed on the protrusion such that the face on which the dividing line is provided contacts the protrusion and the direction of the dividing line is different from the direction of the protrusion, around the axis, when a direction in which the protrusion extends coincides with a direction in which the dividing line extends, the protrusion is fitted into the dividing line. Whereby, the tablet is brought into locking engagement with the protrusion, which prevents further rotation, so that it is possible to align the direction of the dividing line of each tablet in the direction of the protrusion.

Further, the printing device may further include a first image pickup device which picks up an image of the face facing the one side of each tablet while being conveyed and a second image pickup device which picks up an image of the face facing the other side of each tablet while being conveyed. In this case, the dividing line direction aligning section may rotate each tablet while being conveyed around the predetermined axis facing in the orthogonal direction such that the direction of the dividing line becomes the predetermined direction based on at least one of the image pickup results of the first image pickup device and the second image pickup device.

As described above, it is also possible to align the direction of the dividing line of each tablet in a predetermined direction by the dividing line direction aligning section rotating the tablet based on the image pickup result.

In the printer, the first printing device prints a first symbol in a first region at one side with respect to the dividing line or the portion which corresponds to the dividing line and prints a second symbol different from the first symbol in a second region at the other side on the face facing the one side.

The second printing device prints the second symbol in a region corresponding to the first region and prints the first symbol in a region corresponding to the second region on the face facing the other side.

According to the above-described configuration, on the tablet on which printing is performed by the printer, the both symbols of the first symbol and the second symbol are printed at either divided piece when the tablet is divided at the position of the dividing line.

Further, on the tablet according to the above-described embodiment, printing is performed on at least one face out of a face facing the one side and a face facing the other side using any of the printers described above.

DETAILED DESCRIPTION OF THE PREFERRED EMBODIMENT

One embodiment of a printer according to the present invention will be described below with reference to FIG. 1 to FIG. 8. It should be noted that, in the present embodiment, an object on which printing is to be performed is a tablet 1 having a groove-shaped dividing line 11 for dividing the tablet 1 on one face.

Figure 1:
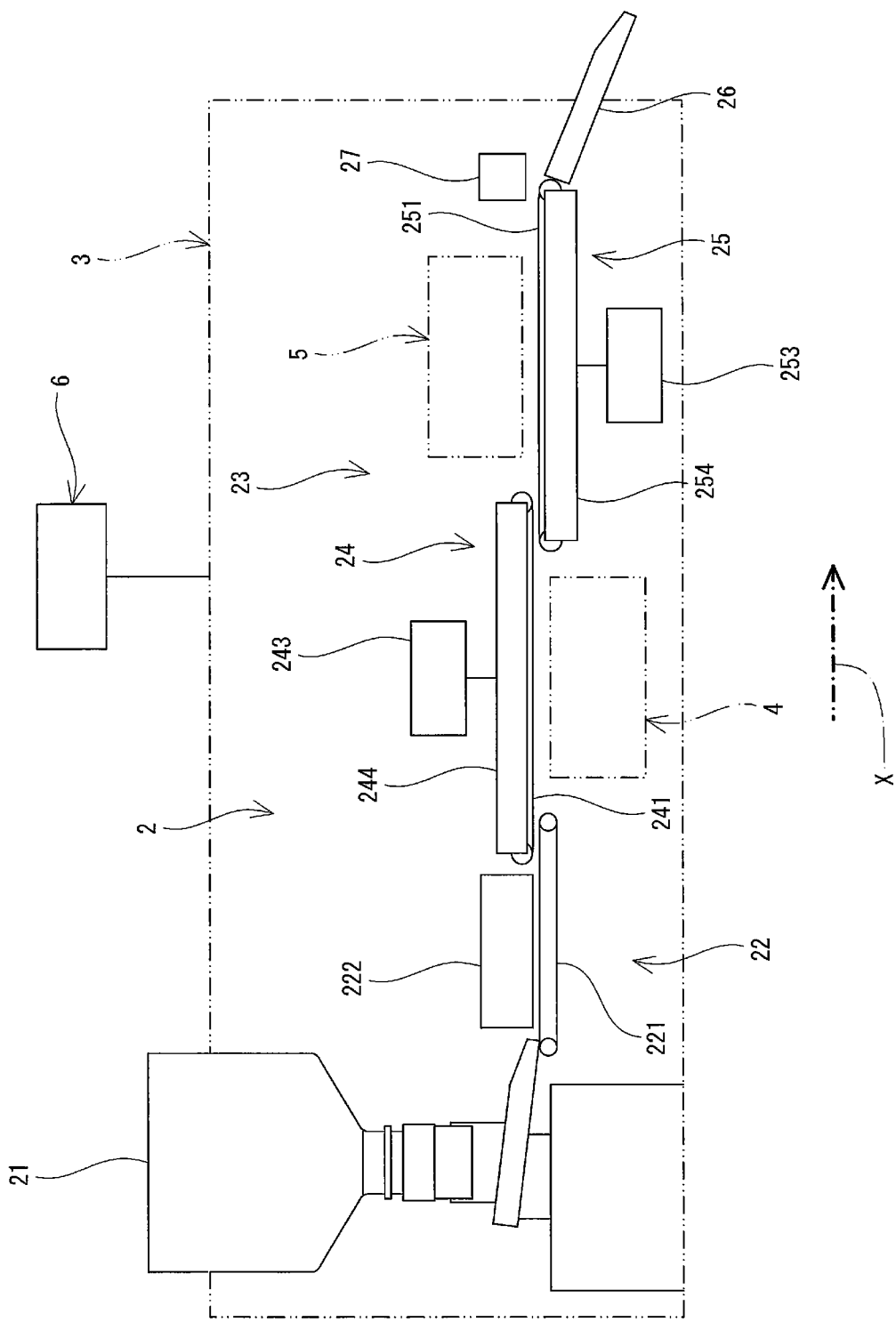
FIG. 1 is an overall front view of a printer according to one embodiment of the present invention.

As illustrated in FIG. 1, the printer according to the present embodiment includes a conveying unit 2 that conveys a tablet 1, a housing 3 that holds the conveying unit 2, a first image pickup printing unit 4 that picks up an image of a face facing one side (lower face in the present embodiment) in an orthogonal direction (up-down direction in FIG. 1) to a conveyance direction (rightward in FIG. 1) of the tablet 1 while being conveyed and performs printing on the face, and a second image pickup printing unit 5 that picks up an image of a face facing the other side (upper face in the present embodiment) in the orthogonal direction of the tablet 1 while being conveyed and performs printing on the face. Further, the printer includes a control unit (control section) 6 that controls each component of the printer and checks the tablet 1.

As illustrated in FIG. 1, the conveying unit 2 includes a storage device 21 that stores tablets 1 supplied from an upstream side, a carrying device 22 that carries the tablets 1 stored in the storage device 21 in an aligned manner, a conveying device 23 that conveys the received tablets 1, and a discharging device 26 that discharges the conveyed tablets 1 to a downstream side. Further, the conveying unit 2 includes a rejecting device 27 that rejects a predetermined tablet 1 so as to prevent the predetermined tablet 1 from discharging from the discharging device 26.

The storage device 21 stores inside the tablets 1 supplied from above and discharges the stored tablets 1 from a lower part. The carrying device 22 includes a carrying belt 221 which has a portion along a direction X in which the tablets 1 are conveyed (hereinafter, referred to as a "conveyance direction") at an upper part and which rotates endlessly, and an aligning section 222 that aligns the tablets 1 placed on the carrying belt 221 in a plurality of lines (four lines in the present embodiment). Whereby, the carrying device 22 can supply the tablets 1 aligned in a plurality of lines to the conveying device 23.

The conveying device 23 includes a first conveying section 24 that conveys the tablets 1 in the conveyance direction X while contacting an upper side of the tablets 1, and a second conveying section 25 which is located at a downstream side of the first conveying section 24 and which conveys the tablets 1 in the conveyance direction X while contacting a lower side of the tablets 1. It should be noted, though not illustrated, a plurality of the conveying devices 23 (for example, four conveying devices 23 in the present embodiment) are aligned according to the number of lines of the tablets 1 aligned at the carrying device 22. In association with this, a plurality of image pickup printing units 4 and 5 (for example, each of four image pickup printing units in the present embodiment) are aligned according to the number of the conveying devices 23.

Figure 2:
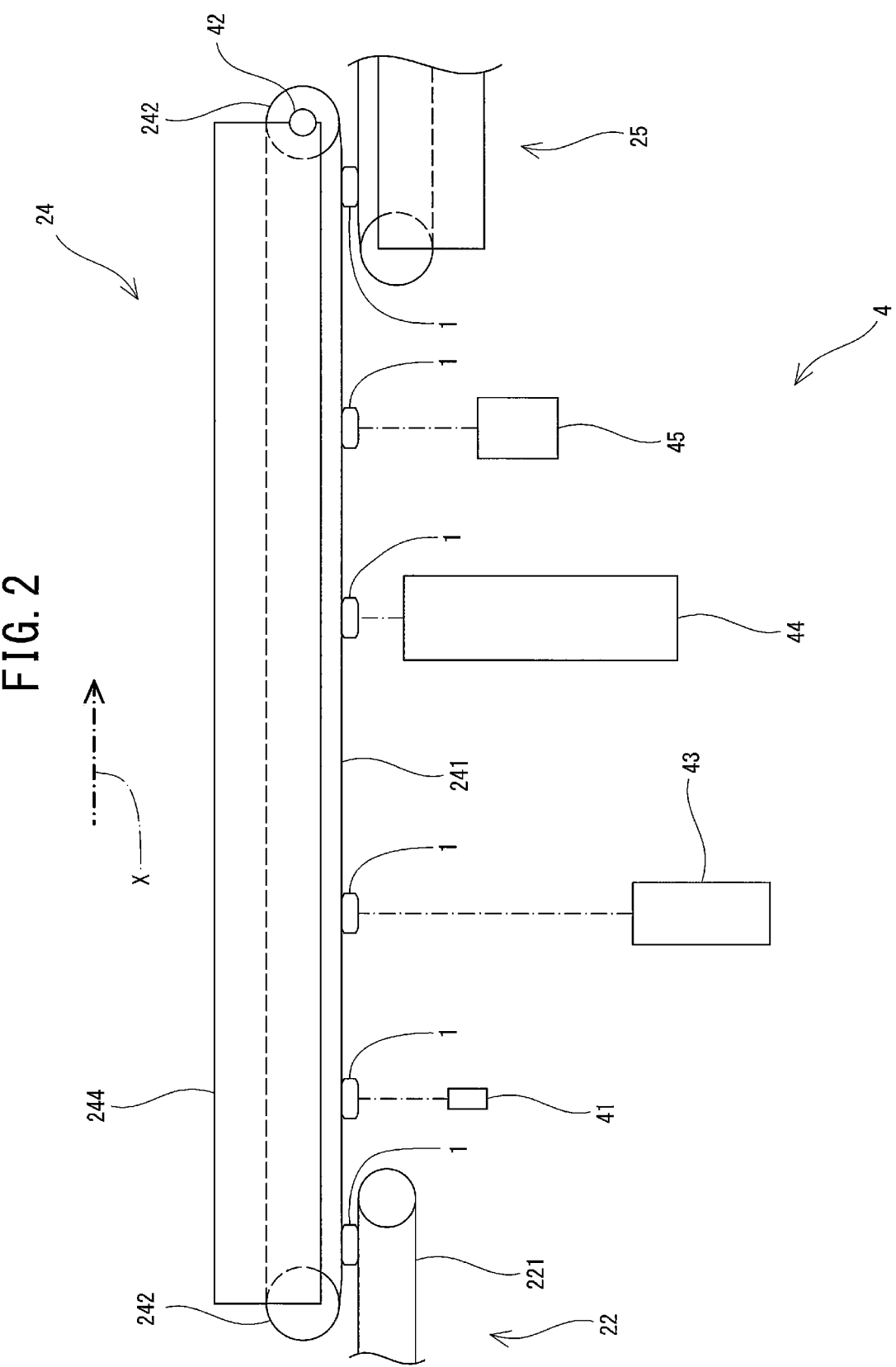
FIG. 2 is a front view of a first conveying section and its surroundings of the printer according to the embodiment.

As illustrated in FIG. 1 and FIG. 2, the first conveying section 24 includes a first conveying belt 241 which has a portion along the conveyance direction X at a lower part and which rotates endlessly, and rotators 242 between which the first conveying belt 241 is hung. Further, the first conveying section 24 includes a suction section 243 for suctioning the tablet 1 and a holding section 244 that holds the first conveying belt 241 to improve suction efficiency.

Whereby, by the suction section 243 suctioning the tablet 1, the first conveying section 24 holds by suction the tablet 1 at the lower part of the first conveying belt 241. The first conveying section 24 conveys the tablet 1 so that the lower face of the tablet 1 is exposed.

Further, the first conveying section 24 is disposed so that an end of the first conveying section 24 at the upstream side vertically overlaps with an end of the conveying device 22 at the downstream side. Whereby, the first conveying section 24 holds by suction the tablet 1 placed on the carrying belt 221 at the lower part of the first conveying belt 241. The conveyance speed of the first conveying section 24 (that is, the running speed of the first conveying belt 241) is higher than the conveyance speed of the carrying device 22 (that is, the running speed of the carrying belt 221). Whereby, the first conveying section 24 can convey the tablets 1, 1 which are carried from the carrying device 22 in a state where they are close to each other, while separating the tablets 1, 1 from each other.

Figure 3:
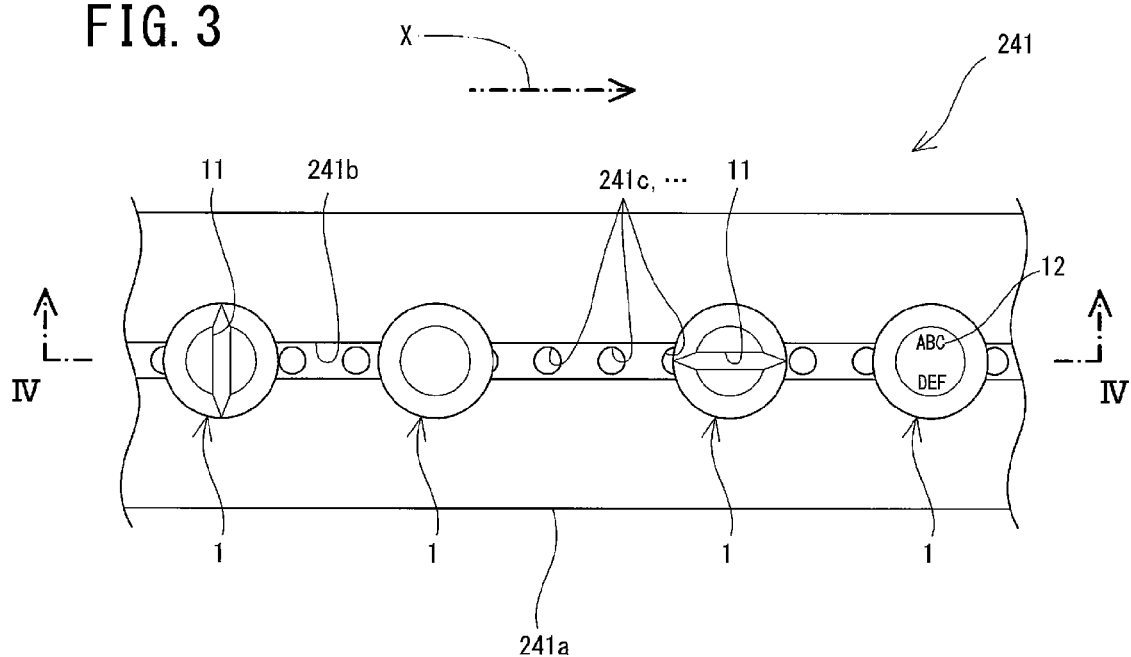
FIG. 3 is a partial enlarged bottom view of the first conveying section of the printer according to the embodiment.
Figure 4:
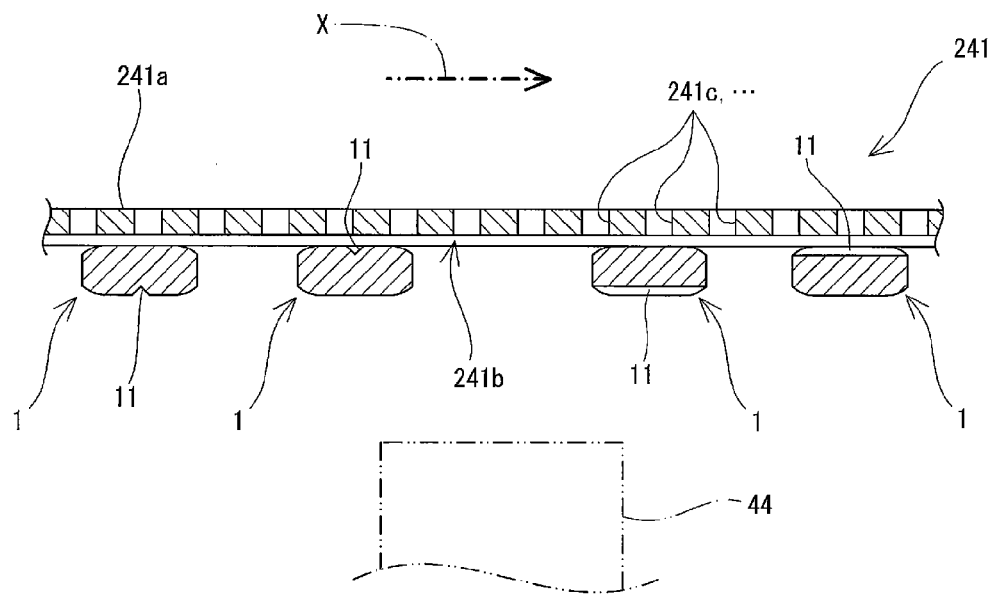
FIG. 4 is a cross-sectional view of the printer according to the embodiment, taken along line IV-IV in FIG. 3.

As illustrated in FIG. 3 and FIG. 4, the first conveying belt 241 includes a belt body 241*a* formed in a band shape, a groove 241*b* which is disposed in the center of a width direction of the belt body 241*a* and which extends along a longitudinal direction, and a plurality of suction holes 241*c* which are disposed at the groove 241*b* and which are aligned along the longitudinal direction. By the suction section 243 suctioning the tablet 1 through the suction hole 241*c* and the groove 241*b*, the first conveying belt 241 holds by suction the tablet 1 at the lower face of the belt body 241*a*.

A width of the groove 241*b* is set smaller than a diameter of the tablet 1. Further, a diameter of the suction hole 241*c* is set smaller than the diameter of the tablet 1. A distance between the suction holes 241*c* is set smaller than the diameter of the tablet 1. Whereby, the tablet 1 vertically overlaps with the plurality of suction holes 241*c*. It should be noted that the configuration of the suction hole 241*c* is not limited to the above-described configuration, and, for example, the suction hole 241*c* may be formed in the shape of an elongate hole along the longitudinal direction.

Figure 5:
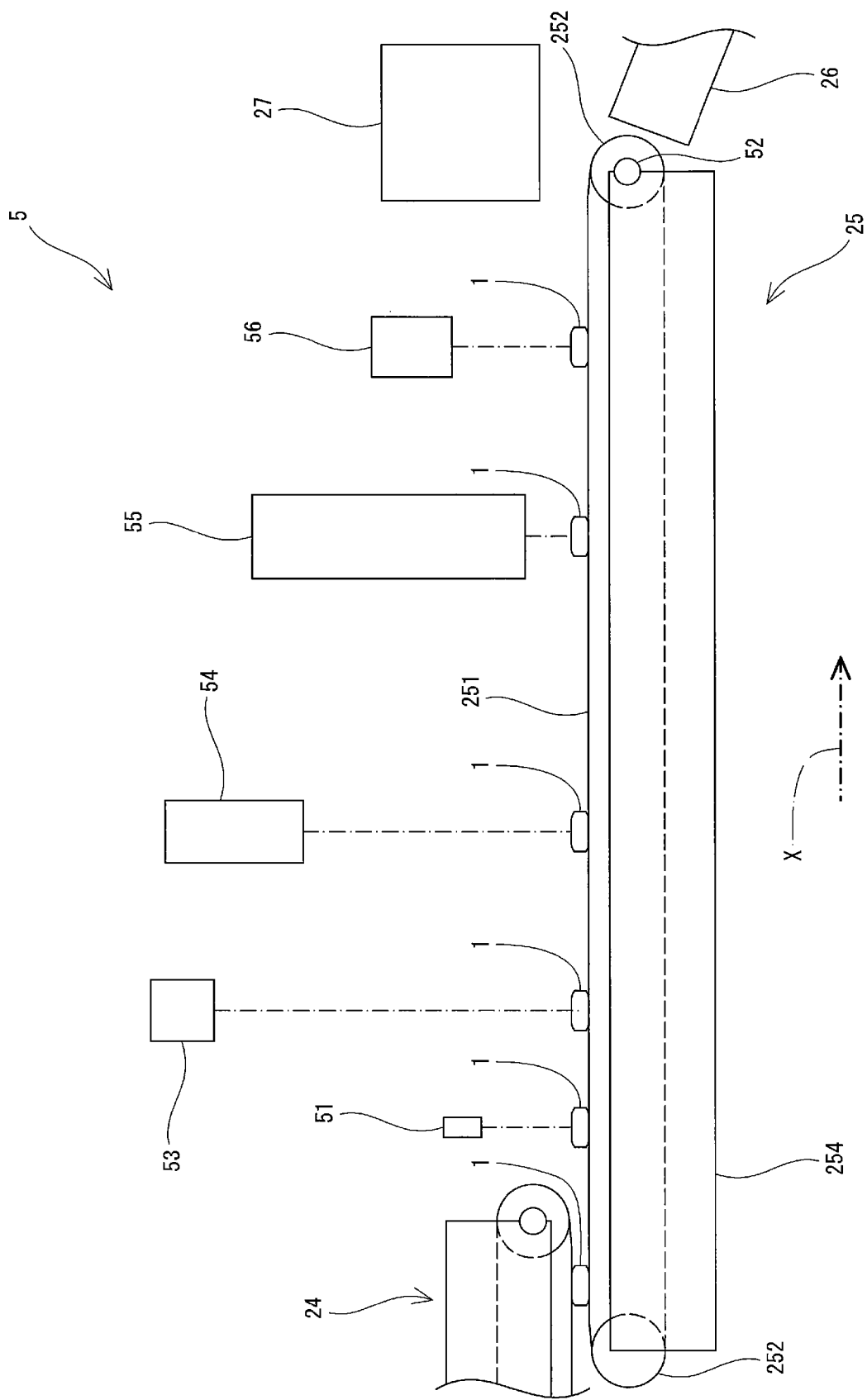
FIG. 5 is a front view of a second conveying section and its surroundings of the printer according to the embodiment.

As illustrated in FIG. 1 and FIG. 5, the second conveying section 25 includes a second conveying belt 251 which has a portion along the conveyance direction X at an upper part and which rotates endlessly, and rotators 252 between which the second conveying belt 251 is hung. Further, the second conveying section 25 includes a suction section 253 for suctioning a tablet 1 and a holding section 254 that holds the second conveying belt 251 to improve suction efficiency.

By the suction section 253 suctioning the tablet 1, the second conveying section 25 holds the tablet 1 by suction at the upper part of the second conveying belt 251. Whereby, the second conveying section 25 conveys the tablet 1 so that an upper face of the tablet 1 is exposed.

Further, the second conveying section 25 is disposed so that an upstream end of the second conveying section 25 vertically overlaps with a downstream end of the first conveying section 24. Whereby, the second conveying section 25 holds by suction the tablet 1 which is held by suction at the lower part of the first conveying belt 241 at the upper part of the second conveying belt 251. The conveyance speed of the second conveying section 25 (that is, the running speed of the second conveying belt 251) is the same as the conveyance speed of the first conveying section 24 (that is, the running speed of the first conveying belt 241). It should be noted that the configuration of the second conveying belt 251 is substantially the same as the configuration of the first conveying belt 241.

The rejecting device 27 rejects a predetermined tablet 1 based on control by the control unit 6. Specifically, the rejecting device 27 prevents the tablet 1 from discharging from the discharging device 26 by ejecting compressed air toward the predetermined tablet 1 when the tablet 1 is transferred from the second conveying section 25 to the discharging device 26.

As illustrated in FIG. 2, the first image pickup printing unit 4 includes a first detecting section 41 that detects the tablet 1 while being conveyed by the first conveying section 24, and a first displacement measuring section 42 that measures an amount of displacement of the tablet 1. The first image pickup printing unit 4 includes a lower image pickup device (also referred to as a "first image pickup device") 43 that picks up an image of a lower face of the tablet 1, a lower printing device (also referred to as a "first printing device") 44 that performs printing on the lower face of the tablet 1, and a lower printed portion image pickup device (also referred to as a "first printed portion image pickup device") 45 that picks up an image of a portion on which printing is performed (hereinafter, referred to as a "printed portion", see FIG. 3) on the lower face of the tablet 1.

The first detecting section 41 detects that the tablet 1 reaches a predetermined reference position of the first conveying section 24. For example, the first detecting section 41 is a photoelectric sensor, or the like. Further, the first displacement measuring section 42 measures an amount of displacement of the tablet 1 by measuring a running amount of the first conveying section 24. For example, the first displacement measuring section 42 is an encoder, or the like, attached to the rotator 242 of the first conveying section 24. Therefore, when the first detecting section 41 detects that the tablet 1 reaches the reference position and the first displacement measuring section 42 measures an amount of displacement from the reference position, the position of the tablet 1 at the first conveying section 24 is detected.

The lower image pickup device 43 is disposed at the downstream side of the first detecting section 41, and below the first conveying section 24. The lower image pickup device 43 picks up an image of the lower face of the tablet 1 based on control by the control unit 6. It should be noted that, though not illustrated, the lower image pickup device 43 includes a light source that emits a light toward the tablet 1, an optical system (such as a lens and a mirror) that radiates and reflects a light reflected on the lower face of the tablet 1 and an image pickup element (such as an area image sensor and a line image sensor) that receives the light which has passed through the optical system.

The lower printing device 44 is disposed at the downstream side of the lower image pickup device 43 and below the first conveying section 24. The lower printing device 44 performs printing on the lower face of the tablet 1 based on the control by the control unit 6. In the present embodiment, the lower printing device 44 is a non-contact type printing mechanism in which the device itself does not contact the tablet 1. For example, the lower printing device 44 is an ink jet printer, or the like, that ejects ink toward the tablet 1.

The lower printed portion image pickup device 45 is disposed at the downstream side of the lower printing device 44 and below the first conveying section 24. The lower printed portion image pickup device 45 picks up an image of a printed portion 12 at the lower side of the tablet 1 based on control by the control unit 6. It should be noted that, though not illustrated, the lower printed portion image pickup device 45 includes a light source that emits a light toward the tablet 1, an optical system that radiates and reflects a light reflected at the lower side of the tablet 1 and an image pickup element that receives the light which has passed through the optical system.

The second image pickup printing unit 5 includes a second detecting section 51 that detects a tablet 1 while being conveyed to the second conveying section 25 and a second displacement measuring section 52 that measures an amount of displacement of the tablet 1. The second image pickup printing unit 5 includes a lateral image pickup device 53 that picks up an image of the lateral side of the tablet 1, an upper image pickup device (also referred to as a "second image pickup device") 54 that picks up an image of the upper face of the tablet 1, an upper printing device (also referred to as a "second printing device") 55 that performs printing on the upper face of the tablet 1, and an upper printed portion image pickup device (also referred to as a "second printed portion image pickup device") 56 that picks up an image of the printed portion 12 at the upper side of the tablet 1.

The second detecting section 51 detects that the tablet 1 reaches a predetermined reference position of the second conveying section 25. Further, the second displacement measuring section 52 measures an amount of displacement of the tablet 1 by measuring a running amount of the second conveying section 25. In this way, when the second detecting section 51 detects that the tablet 1 reaches the reference position and the second displacement measuring section 52 measures the amount of displacement from the reference position, the position of the tablet 1 at the second conveying section 25 is detected.

The lateral image pickup device 53 is disposed at the downstream side of the second detecting section 51 and above the second conveying section 25. The lateral image pickup device 53 picks up an image of the lateral face of the tablet 1 based on control by the control unit 6. It should be noted that, though not illustrated, the lateral image pickup device 53 includes a light source that emits a light toward the tablet 1, an optical system that radiates and reflects a light reflected at the lateral side of the tablet 1, and an image pickup element that receives the light which has passed through the optical system.

The upper image pickup device 54 is disposed at the downstream side of the lateral image pickup device 53 and above the second conveying section 25. The upper image pickup device 54 picks up an image of the upper face of the tablet 1 based on control by the control unit 6. It should be noted that, though not illustrated, the upper image pickup device 54 includes a light source that emits a light toward the tablet 1, an optical system that radiates and reflects a light reflected at the upper face of the tablet 1, and an image pickup element that receives the light which has passed through the optical system.

The upper printing device 55 is disposed at the downstream side of the upper image pickup device 54 and above the second conveying section 25. The upper printing device 55 performs printing on the upper face of the tablet 1 based on control by the control unit 6. In the present embodiment, the upper printing device 55 is a non-contact type printing mechanism (such as an ink jet printer) in which the upper printing device 55 itself does not contact the tablet 1.

The upper printed portion image pickup device 56 is disposed at the downstream side of the upper printing device 55 and above the second conveying section 25. The upper printed portion image pickup device 56 picks up an image of the printed portion 12 on the upper face of the tablet 1 based on control by the control unit 6. It should be noted that, though not illustrated, the upper printed portion image pickup device 56 includes a light source that emits a light toward the tablet 1, an optical system that radiates and reflects a light reflected on the upper face of the tablet 1, and an image pickup element that receives the light which has passed through the optical system.

Figure 6:
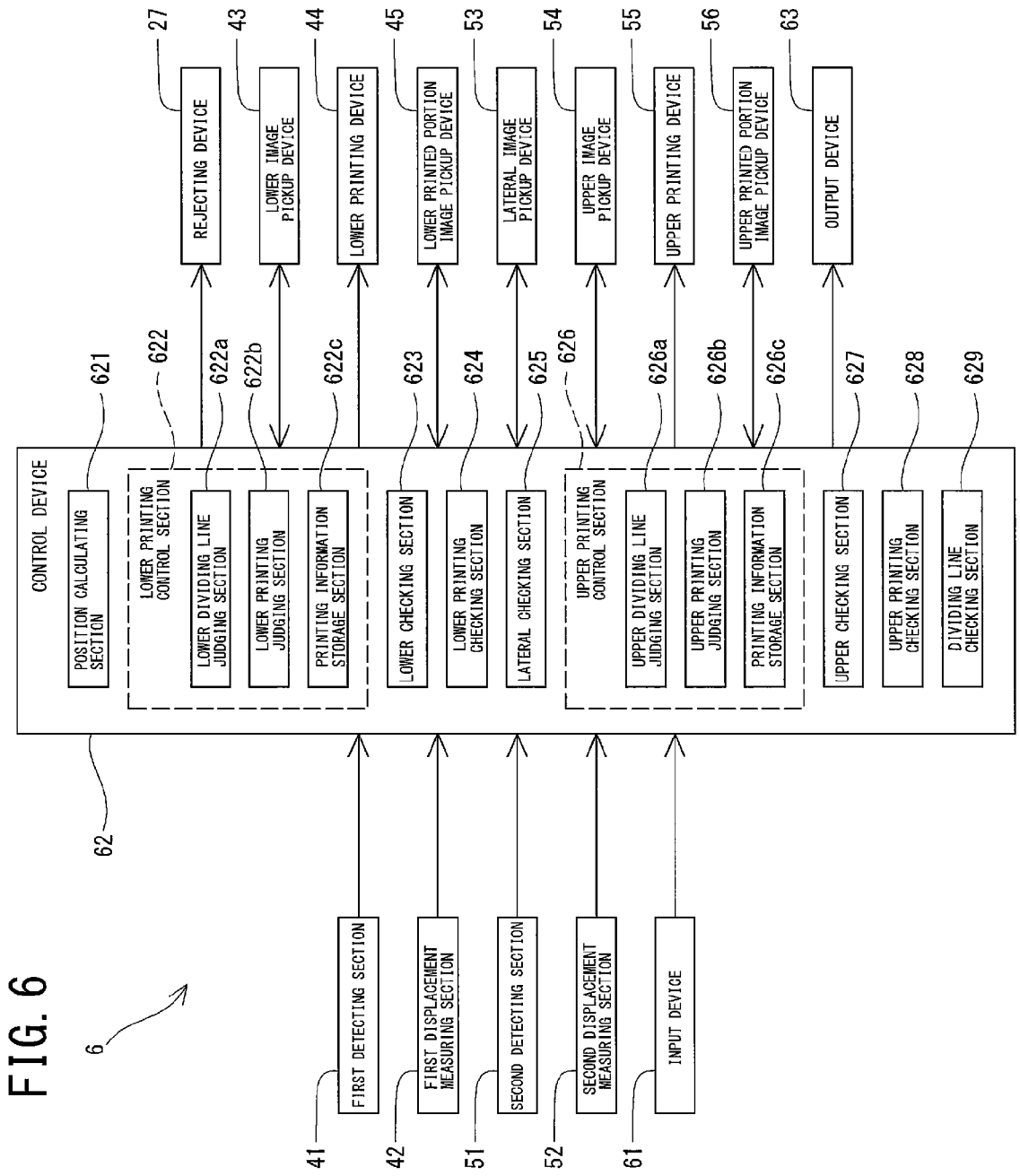
FIG. 6 is a block diagram of the printer according to the embodiment.

As illustrated in FIG. 6, the control unit 6 includes an input device 61 that inputs each information, a control device 62 that controls each device, and an output device 63 that outputs each information.

The input device 61 inputs information of a target tablet 1, which is to be checked and printed, to the control device 62. For example, the input device 61 is a keyboard (numerical keypad), a select switch, or the like. When the information (such as a number according to a type) of the tablet 1 is input to the control device 62 through the input device 61, the control device 62 recognizes the information (such as the information on whether or not there is a dividing line 11, and the shape) of the target tablet 1. The control device 62 includes a position calculating section 621 that calculates the position of the tablet 1, a lower printing control section (also referred to as a "first printing control section") 622 that controls the lower printing device 44, a lower checking section (also referred to as a "first checking section") 623 that checks the lower side of the tablet 1, and a lower printing checking section 624 that checks the printed portion 12 at the lower side of the tablet 1. Further, the control device 62 includes a lateral checking section 625 that checks the lateral side of the tablet 1.

The control device 62 includes an upper printing control section (also referred to as a "second printing control section") 626 that controls the upper printing device 55, an upper checking section (also referred to as a "second checking section") 627 that checks the upper face of the tablet 1, and an upper printing checking section 628 that checks the printed portion 12 on the upper face of the tablet 1. Further, the control device 62 includes a dividing line checking section 629 that checks the judgment result as to whether or not there is a dividing line 11.

The position calculating section 621 calculates the position of the tablet 1 based on the information from the detecting sections 41 and 51 and the displacement measuring sections 42 and 52. The control device 62 makes each of the image pickup devices 43, 45, 53, 54 and 56 pick up an image of the tablet 1 at a predetermined timing based on the result calculated at the position calculating section 621 and makes each of the printing devices 44 and 55 perform printing on the tablet 1 at a predetermined timing.

The lower printing control section 622 includes a lower dividing line judging section (also referred to as a "first dividing line judging section") 622a that judges whether or not there is a dividing line 11 on the lower face of the tablet 1 based on the image picked up at the lower image pickup device 43, and a lower printing judging section (also referred to as a "first printing judging section") 622b that judges whether or not to perform printing on the lower face of the tablet 1 based on the image picked up by the lower image pickup device 43. Further, the lower printing control section 622 includes a printing information storage section 622c that stores printing information.

The lower dividing line judging section 622a judges whether or not there is a dividing line 11 from the image picked up by the lower image pickup device 43. Specifically, the lower dividing line judging section 622a judges whether "there is a dividing line" or "there is no dividing line" by comparing stored reference image information with information of the image picked up by the lower image pickup device 43.

The lower printing judging section 622b performs judgment based on the judgment result of the lower dividing line judging section 622a. Specifically, when the lower dividing line judging section 622a judges that "there is no dividing line", the lower printing judging section 622b judges that the lower printing device 44 may "perform printing" on the lower face of the tablet 1. Conversely, when the lower dividing line judging section 622a judges that "there is a dividing line", the lower printing judging section 622b judges that the lower printing device 44 should "not perform printing" on the lower face of the tablet 1.

The lower checking section 623 checks the lower face of the tablet 1 based on the image picked up by the lower image pickup device 43. Specifically, the lower checking section 623 judges whether the lower face of the tablet 1 is "normal" or "abnormal" by comparing the stored reference image information with information of the image picked up by the lower image pickup device 43. It should be noted that, though not illustrated, the lower checking section 623 includes a shape checking section that checks whether or not the size is appropriate, a foreign substance checking section that checks whether or not there is a foreign substance, a crack checking section that checks whether or not there is a crack or chipped portion, and the like.

The lower printing checking section 624 checks the printed portion 12 on the lower face of the tablet 1 based on the image picked up by the lower printed portion image pickup device 45. Specifically, the lower checking section 623 judges whether the printed portion 12 of the tablet 1 is "normal" or "abnormal" by comparing the stored reference image information with information of the image picked up by the lower printed portion image pickup device 45.

The lateral checking section 625 checks the lateral side of the tablet 1 based on the image picked up by the lateral image pickup device 53. Specifically, the lateral checking section 625 judges whether the lateral side of the tablet 1 is "normal" or "abnormal" by comparing the stored reference image information with information of the image picked up by the lateral image pickup device 53. It should be noted that, though not illustrated, the lateral checking section 625 includes a shape checking section, a foreign substance checking section, a crack checking section, and the like.

The upper printing control section 626 includes an upper dividing line judging section (also referred to as a "second dividing line judging section") 626a that judges whether or not there is a dividing line 11 on the upper face of the tablet 1 based on the image picked up by the upper image pickup device 54, and an upper printing judging section (also referred to as a "second printing judging section") 626b that judges whether or not to perform printing on the upper face of the tablet 1 based on the image picked up by the upper image pickup device 54. Further, the upper printing control section 626 includes a printing information storage section 626c that stores printing information.

The upper dividing line judging section 626a judges whether or not there is a dividing line 11 based on the image picked up by the upper image pickup device 54. Specifically, the upper dividing line judging section 626a judges whether "there is a dividing line" or "there is no dividing line" by comparing the stored reference image information with information of the image picked up by the upper image pickup device 54.

The upper printing judging section 626b performs judgment based on the judgment result of the upper dividing line judging section 626a. Specifically, when the upper dividing line judging section 626a judges that "there is no dividing line", the upper printing judging section 626b judges that the upper printing device 55 may "perform printing" on the upper face of the tablet 1. Conversely, when the upper dividing line judging section 626a judges that "there is a dividing line", the upper printing judging section 626b judges that the upper printing device 44 should "not perform printing" on the upper face of the tablet 1.

The upper checking section 627 checks the upper face of the tablet 1 based on the image picked up by the upper image pickup device 54. Specifically, the upper checking section 627 judges whether the upper face of the tablet 1 is "normal" or "abnormal" by comparing the stored reference image information with information of the image picked up by the upper image pickup device 54. It should be noted that, though not illustrated, the upper checking section 627 includes a shape checking section, a foreign substance checking section, a crack checking section, and the like.

The upper printing checking section 628 checks the printed portion 12 on the upper face of the tablet 1 based on the image picked up by the upper printed portion image pickup device 56. Specifically, the upper printing checking section 628 judges whether the printed portion 12 of the tablet 1 is "normal" or "abnormal" by comparing the stored reference image information with information of the image picked up by the upper printed portion image pickup device 56.

The dividing line checking section 629 checks the judgment results of the dividing line judging sections 622a and 626a based on the judgment result of the lower dividing line judging section 622a and the judgment result of the upper dividing line judging section 626a. Specifically, the dividing line checking section 629 judges a case where the judgment results of the dividing line judging sections 622a and 626a are different from each other ("there is a dividing line" and "there is no dividing line") as "normal". Meanwhile, the dividing line checking section 629 judges a case where the judgment results of the dividing line judging sections 622a and 626a are the same ("there is a dividing line" and "there is a dividing line", or "there is no dividing line" and "there is no dividing line") as "abnormal".

The output device 63 outputs images which are picked up by the image pickup devices 43, 45, 53, 54 and 56 and stored in the control device 62, and the check results of the checking sections 623, 624, 625, 627, 628 and 629, the counting results, or the like. For example, the output device 63 is a monitor, a printer, or the like.

Figure 7:
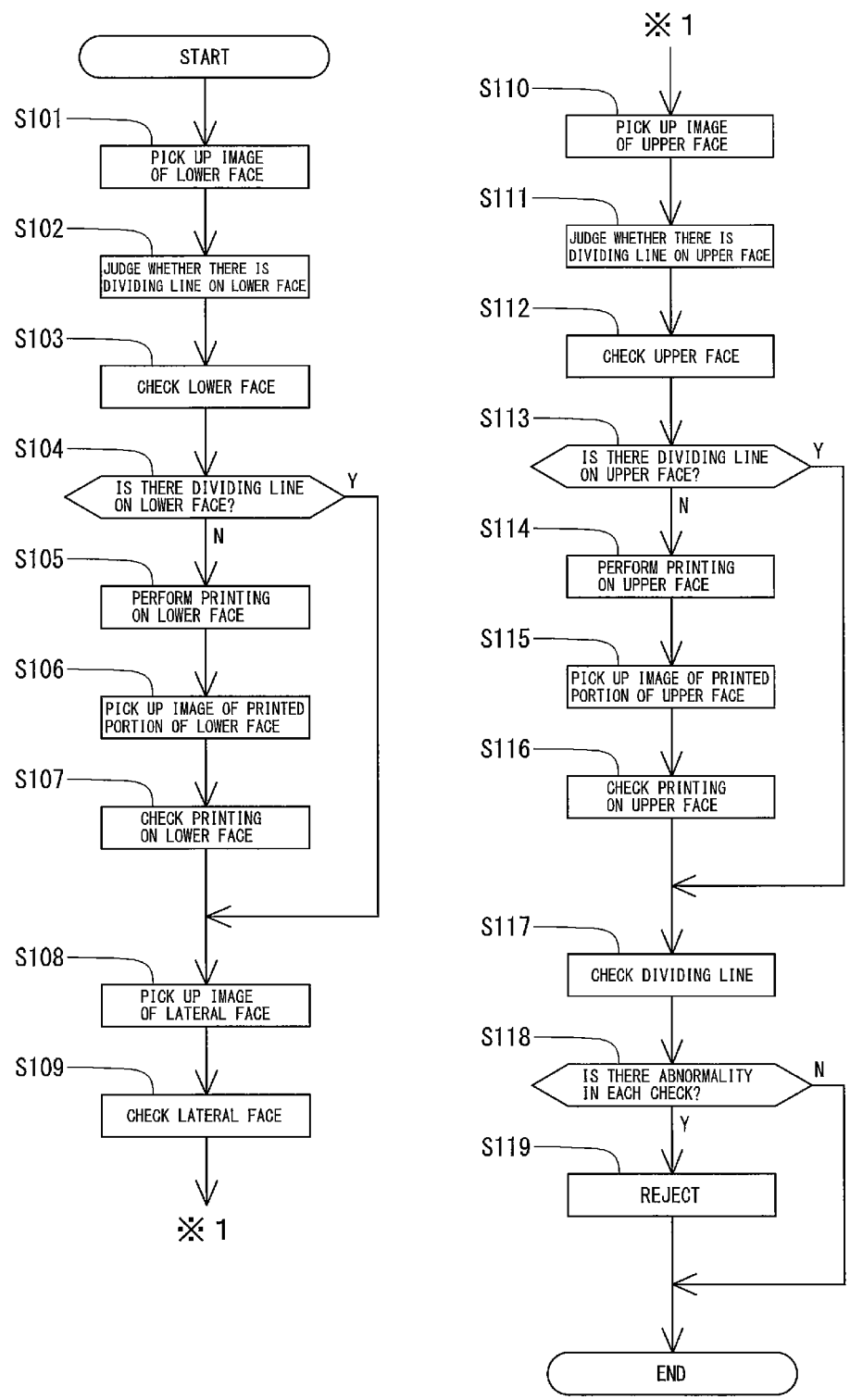
FIG. 7 is a flowchart of the printer according to the embodiment.

Next, a method for manufacturing a tablet 1 using the printer according to the present embodiment will be described below with reference to FIG. 7. It should be noted that an object on which printing is to be performed is a tablet 1 having a dividing line 11 for dividing the tablet 1 on one face.

First, the lower image pickup device 43 picks up an image of the lower face of the tablet 1 which is being conveyed by the first conveying section 24 (step 101). Then, the lower dividing line judging section 622a judges whether or not there is a dividing line 11 based on the image picked up by the lower image pickup device 43 (step 102). Then, the lower checking section 623 checks whether the lower face of the tablet 1 is normal or abnormal based on the image picked up by the lower image pickup device 43 (step 103).

When there is no dividing line 11 on the lower face of the tablet 1 (step 104: "N"), the lower printing device 44 performs printing on the lower face of the tablet 1 while being conveyed (step 105). Subsequently, the lower printed portion image pickup device 45 picks up an image of the printed portion 12 on the lower face of the tablet 1 while being conveyed (step 106). Then, the lower printing checking section 624 checks whether the printed portion 12 is normal or abnormal based on the image picked up by the lower printed portion image pickup device 45 (step 107). Conversely, when there is a dividing line 11 on the lower face of the tablet 1 (step 104: "Y"), the tablet 1 is conveyed without being subjected to printing, image pickup or check.

When the tablet 1 is transferred from the first conveying section 24 to the second conveying section 25, the lateral image pickup device 53 picks up an image of the lateral side of the tablet 1 while being conveyed (step 108). Then, the lateral checking section 625 checks whether the lateral side of the tablet 1 is normal or abnormal based on the image picked up by the lateral image pickup device 53 (step 109).

The upper image pickup device 54 picks up an image of the upper face of the tablet 1 while being conveyed by the second conveying section 25 (step 110). Then, the upper dividing line judging section 626a judges whether there is a dividing line 11 based on the image picked up by the upper image pickup device 54 (step 111). Subsequently, the upper checking section 627 checks whether the upper face of the tablet 1 is normal or abnormal based on the image picked up by the upper image pickup device 54 (step 112).

When there is no dividing line 11 on the upper face of the tablet 1 (step 113: "N"), the upper printing device 55 performs printing on the upper face of the tablet 1 while being conveyed (step 114). Subsequently, the upper printed portion image pickup device 56 picks up an image of the printed portion 12 on the upper face of the tablet 1 while being conveyed (step 115). Then, the upper printing checking section 628 checks whether the printed portion 12 is normal or abnormal based on the image picked up by the upper printed portion image pickup device 56 (step 116). Conversely, when there is a dividing line 11 on the upper face of the tablet 1 (step 113: "Y"), the tablet 1 is conveyed without being subjected to printing, image pickup or check.

The dividing line checking section 629 checks whether the judgment results of the dividing line judging sections 622a and 626a are normal or abnormal based on the judgment results of the dividing line judging sections 622a and 626a (step 117). Then, when the checking results of the checking sections 623, 624, 625, 627, 628 and 629 include at least one result indicating abnormal (step 118: "Y"), the rejecting device 27 rejects the tablet 1 while being conveyed (step 119). Conversely, when all the checking results of the checking sections 623, 624, 625, 627, 628 and 629 are normal (step 118: "N"), the tablet 1 is conveyed to the discharging device 26 without being rejected.

Figure 8:
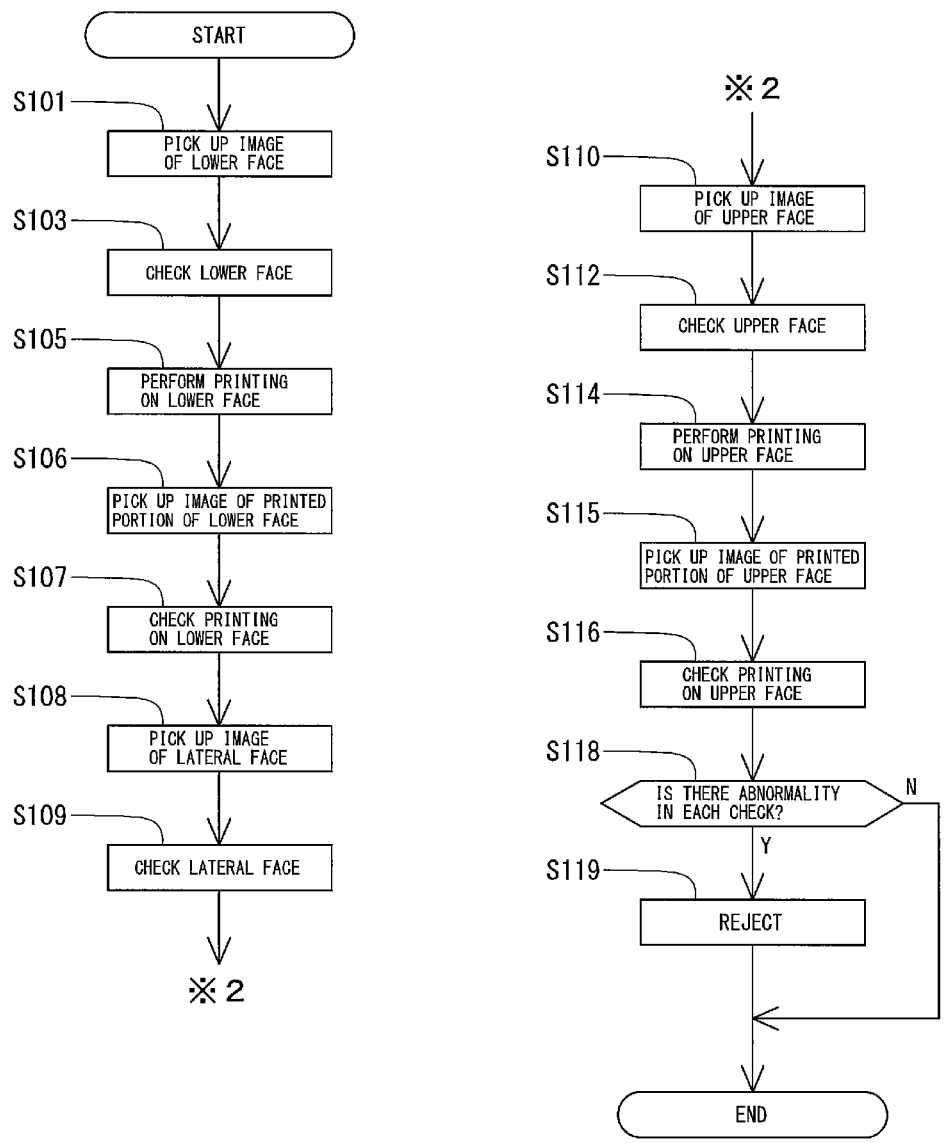
FIG. 8 is a flowchart of the printer according to the embodiment.

Next, another method for manufacturing a tablet 1 using the printer according to the present embodiment will be described below with reference to FIG. 8. It should be noted that an object on which printing is to be performed is a tablet 1 which does not have a dividing line 11.

Because the object is a tablet 1 which does not have a dividing line 11, judgment as to whether or not there is a dividing line performed by the lower dividing line judging section 622a (steps 102 and 104), judgment as to whether or not there is a dividing line performed by the upper dividing line judging section 626a (steps 111 and 113), and checking of the judgment results of the dividing line judging sections 622a and 626a performed by the dividing line checking section 629 (step 117) are not performed. Because the steps 101, 103, 105 to 110, 112, 114 to 116 and 118 to 119 are as described above, the explanation will be omitted.

According to the printer of the present embodiment, the conveying device 23 conveys the tablet 1. The lower image pickup device 43 picks up an image of the lower face of the tablet 1 while being conveyed. Then, the lower checking section 623 checks the lower face of the tablet 1 based on the image picked up by the lower image pickup device 43. Further, the upper image pickup device 54 picks up an image of the upper face of the tablet 1 while being conveyed. Then, the upper checking section 627 checks the upper face of the tablet 1 based on the image picked up by the upper image pickup device 54.

Further, the lower printing device 44 disposed at the downstream side of the lower image pickup device 43 performs printing on the lower face of the tablet 1 while being conveyed, and the upper printing device 55 disposed at the downstream side of the upper image pickup device 54 performs printing on the upper face of the tablet 1 while being conveyed. Whereby, the printer can check the both faces of the tablet 1 while being conveyed. Further, the printer can perform printing on the both faces of the tablet 1 while being conveyed or perform printing on a desired one face out of the upper face and the lower face of the tablet 1 while being conveyed.

Further, according to the printer of the present embodiment, the lower printing judging section 622b judges whether or not to perform printing on the lower face of the tablet 1 based on the image picked up by the lower image pickup device 43, and the upper printing judging section 626b judges whether or not to perform printing on the upper face of the tablet 1 based on the image picked up by the upper image pickup device 54. Whereby, the printer can perform printing on the both faces of the tablet 1 while being conveyed or can perform printing on a desired one face out of the upper face and the lower face of the tablet 1 while being conveyed based on the judgment of the printing judging sections 622b and 626b.

Further, in the printer according to the present embodiment, the conveying device 23 conveys the tablet 1 having a dividing line 11 for dividing the tablet 1 on either a face of one side or a face of the other side. Further, the lower dividing line judging section 622a judges whether or not there is a dividing line 11 based on the image picked up by the lower image pickup device 43. When the lower dividing line judging section 622a judges that "there is a dividing line", the lower printing judging section 622b judges "not to perform printing" on the lower face of the tablet 1.

Further, the upper dividing line judging section 626a judges whether or not there is a dividing line 11 based on the image picked up by the upper image pickup device 54. When the upper dividing line judging section 626a judges that "there is a dividing line", the upper printing judging section 626b judges "not to perform printing" on the upper face of the tablet 1. Whereby, the printer can prevent printing on a face having a dividing line 11 of the tablet 1 while being conveyed. That is, the printer can reliably perform printing on a face which does not have a dividing line 11.

Further, according to the printer of the present embodiment, the dividing line checking section 629 judges a case where the judgment results of the dividing line judging sections 622a and 626a are different from each other as "normal". Meanwhile, the dividing line checking section 629 judges a case where the judgment results of the dividing line judging sections 622a and 626a are the same as "abnormal". Whereby, the printer judges the tablet 1 as abnormal when both the dividing line judging sections 622a and 626a judge that "there is a dividing line (or there is no dividing line)", for example, when the judgment results of the dividing line judging section 622a and 626b are wrong, or, when a tablet 1 having dividing lines 11 on the both faces (or a tablet 1 having a dividing line 11 on neither face) is conveyed.

It should be noted that the printer and the tablet according to the present invention are not limited to the above-described embodiments, and, of course, can be modified in various manner within the scope not departing from the spirit of the present invention. Further, it is, of course, possible to arbitrarily select configurations, methods, or the like, according to various modified examples described below and employ them in the configuration, method, or the like according to the above-described embodiments.

For example, the printer according to the present invention may be configured such that, when the first checking section (lower checking section) 623 judges the lower side as abnormal, the first printing judging section (lower printing judging section) 622b judges not to perform printing on a face facing one side (lower side) of the object (tablet) 1, and, when the second checking section (upper checking section) 627 judges the upper side as abnormal, the second printing judging section (upper printing judging section) 626b judges not to perform printing on a face facing the other side (upper side) of the object (tablet) 1.

According to the above-described configuration, the first checking section (lower checking section) 623 judges whether the lower side is normal or abnormal based on the image picked up by the first image pickup device (lower image pickup device) 43. When the first checking section (lower checking section) 623 judges that the lower side is abnormal, the first printing judging section (lower printing judging section) 622b judges not to perform printing on a face facing the one side (lower side) of the object (tablet) 1.

Further, the second checking section (upper checking section) 627 judges whether the upper side is normal or abnormal based on the image picked up by the second image pickup device (upper image pickup device) 54. When the second checking section (upper checking section) 627 judges that the upper side is abnormal, the second printing judging section (upper printing judging section) 626b judges not to perform printing on a face facing the other side (upper side) of the object (tablet) 1. Whereby, the printer can prevent printing on the object (tablet) 1 judged as abnormal in the checking sections 623 and 627.

Figure 10:
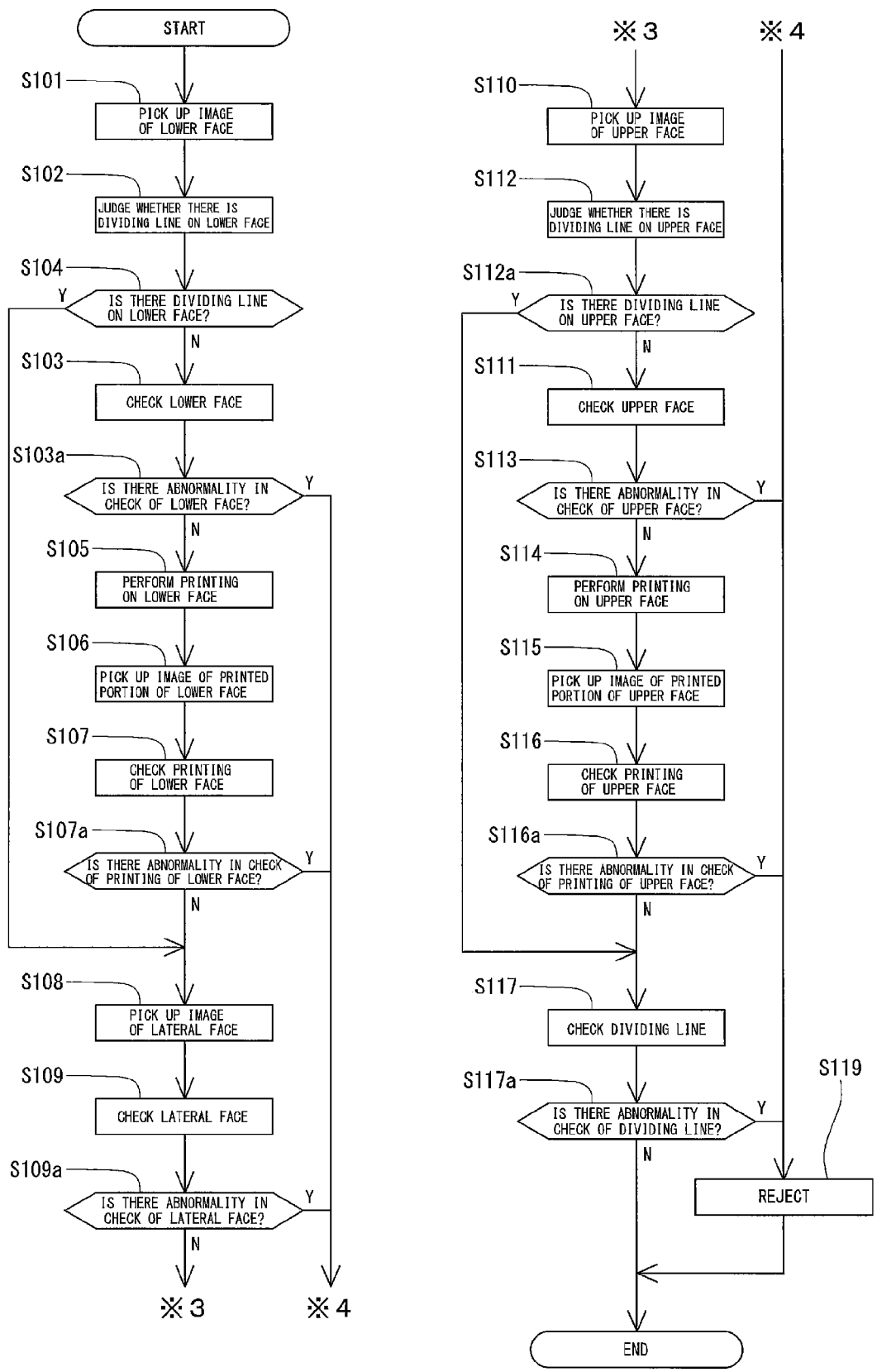
FIG. 10 is a flowchart of the printer according to the embodiment.
Figure 11:
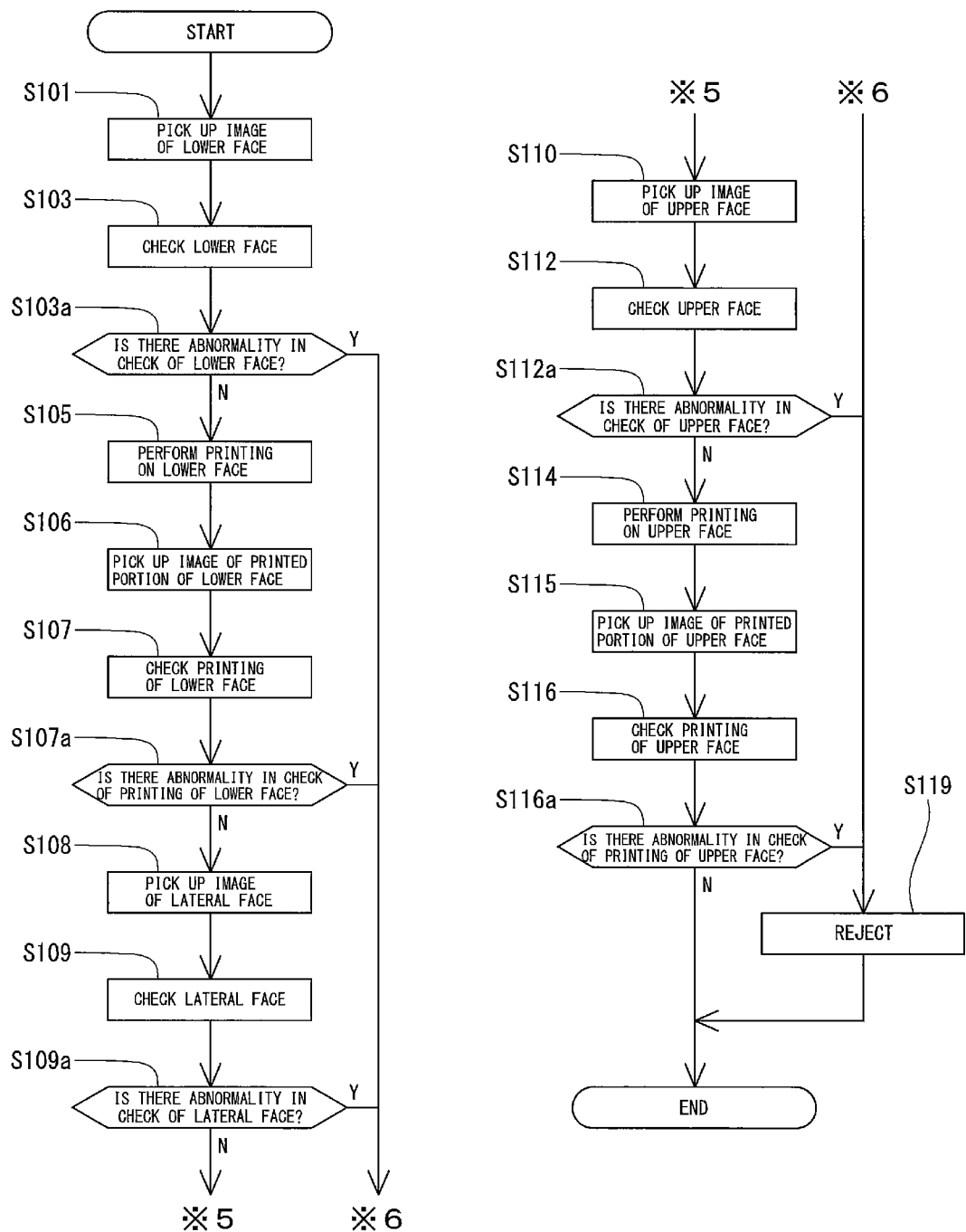
FIG. 11 is a flowchart of the printer according to the embodiment.

An example of the printer having the above-described configuration will be described below with reference to FIG. 9 to FIG. 11.

Figure 9:
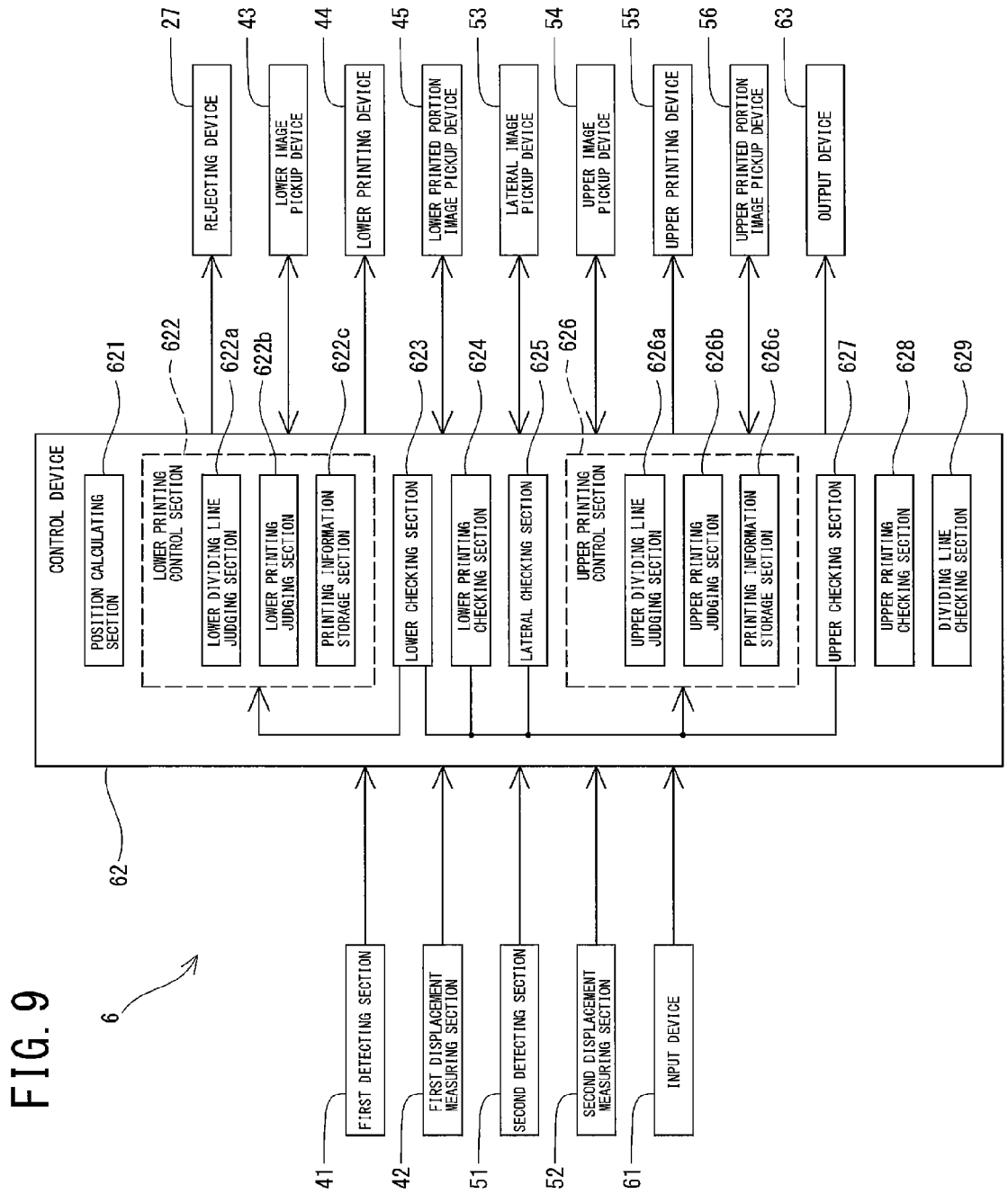
FIG. 9 is a block diagram of a printer according to another embodiment of the present invention.

The printer illustrated in FIG. 9 is configured to stop implementation of image pickup, check, judgment and printing on the tablet 1 which has been determined to be rejected by the rejecting device 27 after determination. It should be noted that each of the checking sections 623, 625 and 627 sequentially performs check of the shape, check of a foreign substance and check of a crack or chipped portion. However, each of the checking sections 623, 625 and 627 is configured to stop implementation of the remaining check after judging that the tablet 1 is abnormal through given check.

The tablet 1 which has been determined to be rejected by the rejecting device 27 is rejected regardless of the check results and judgment results after the determination. Therefore, in the printer illustrated in FIG. 9, image pickup, check, judgment and printing are not performed for the tablet 1 which has been determined to be rejected, so that it is possible to reduce a processing time required for check and judgment, ink required for printing, or the like.

In the printer illustrated in FIG. 9, the lower printing judging section 622b performs judgment based on the judgment results of the lower dividing line judging section 622a and the lower checking section 623. Specifically, in any one of cases where the lower dividing line judging section 622a judges that "there is a dividing line" and where the lower checking section 623 judges that the lower side is abnormal, the lower printing judging section 622b judges that the lower printing device 44 should "not perform printing" on the lower face of the tablet 1.

Further, the upper printing judging section 626b performs judgment based on the judgment results of the lower checking section 623, the lower printing checking section 624, the lateral checking section 625, the upper dividing line judging section 626a and the upper checking section 627. Specifically, in any one of cases where the upper dividing line judging section 626a judges that "there is a dividing line", where the lower checking section 623 judges that the lower side is abnormal, where the lower printing checking section 624 judges that the printed portion is abnormal, where the lateral checking section 625 judges that the lateral side is abnormal, and where the upper checking section 627 judges that the upper side is abnormal, the upper printing judging section 626b judges that the upper printing device 55 should "not perform printing" on the upper face of the tablet 1.

Next, a method for manufacturing a tablet 1 using the printer illustrated in FIG. 9 will be described below with reference to FIG. 10. It should be noted that an object on which printing is to be performed is a tablet 1 having a dividing line 11 for dividing the tablet 1 on one face.

The printer illustrated in FIG. 9 is different from the printer according to the above-described embodiments in that, in the printer illustrated in FIG. 9, after the lower dividing line judging section 622a judges whether or not there is a dividing line 11 based on the image picked up by the lower image pickup device 43 (step 102), the lower checking section 623 checks whether the lower face of the tablet 1 is normal or abnormal based on the image picked up by the lower image pickup device 43 (step 103), and in that, after the upper dividing line judging section 626a judges whether or not there is a dividing line 11 based on the image picked up by the upper image pickup device 54 (step 111), the upper checking section 627 checks whether the upper face of the tablet 1 is normal or abnormal based on the image picked up by the upper image pickup device 54 (step 112).

Further, when each of the checking sections 623, 624, 625, 627 and 628 judges that the tablet 1 is abnormal (steps 103a, 107a, 109a, 112a, 116a and 117a: "Y"), image pickup, check, judgment and printing after the judgment are stopped for the tablet 1. The tablet 1 is then rejected by the rejecting device 27 (step 119). It should be noted that because steps 101 to 117 and 119 are substantially the same as those according to the above-described embodiments, the explanation thereof will be omitted.

Next, another method for manufacturing a tablet 1 using the printer illustrated in FIG. 9 will be described below with reference to FIG. 11. It should be noted that an object on which printing is to be performed is a tablet 1 which does not have a dividing line 11.

Because the object is a tablet 1 which does not have a dividing line 11, judgment as to whether there is a dividing line performed by the lower dividing line judging section 622a (steps 102 and 104), judgment as to whether there is a dividing line performed by the upper dividing line judging section 626a (steps 111 and 113), and check of the judgment results of the dividing line judging section 622a and 626a performed by the dividing line checking section 629 (steps 117 and 117a) are not performed. It should be noted that steps 103a, 107a, 109a, 112a, 116a and 117a are as described above, the explanation thereof will be omitted. Further, steps 101, 103, 105 to 110, 112, 114 to 116 and 119 are substantially the same as those according to the above-described embodiments, the explanation thereof will be omitted.

Further, in the printer according to the above-described embodiments, a distance between the suction holes 241c is set smaller than the diameter of the tablet 1. However, the printer according to the present invention is not limited to the above-described configuration. For example, as illustrated in FIG. 12 and FIG. 13, the distance between the suction holes 241c may be set larger than the diameter of the tablet 1.

Figure 12:
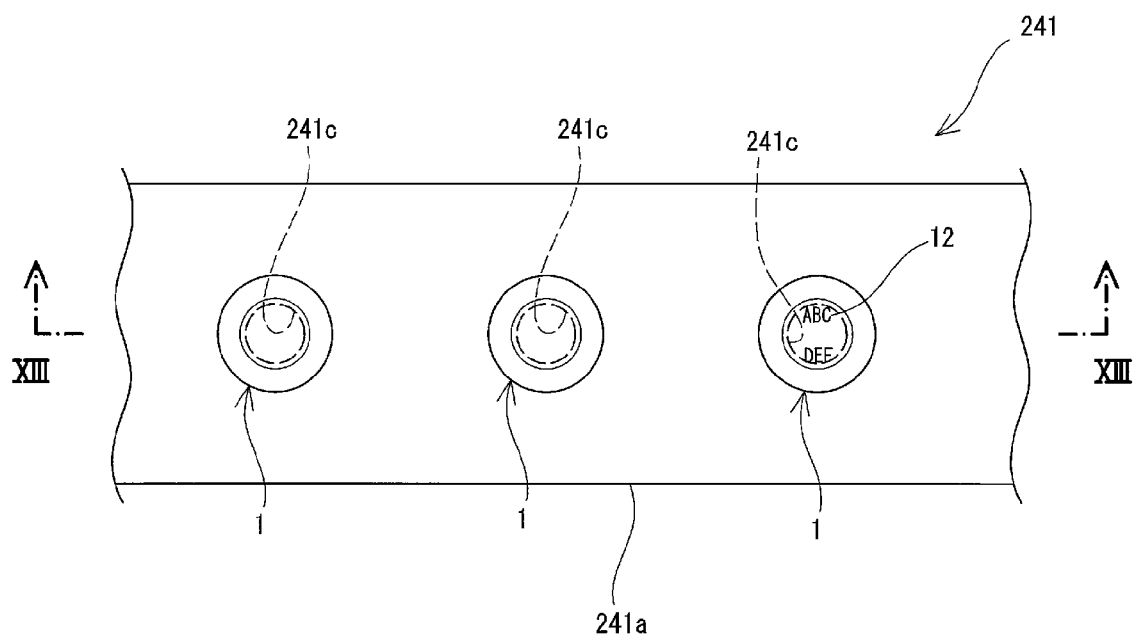
FIG. 12 is a partial enlarged bottom view of a first conveying section of a printer according to still another embodiment of the present invention.
Figure 13:
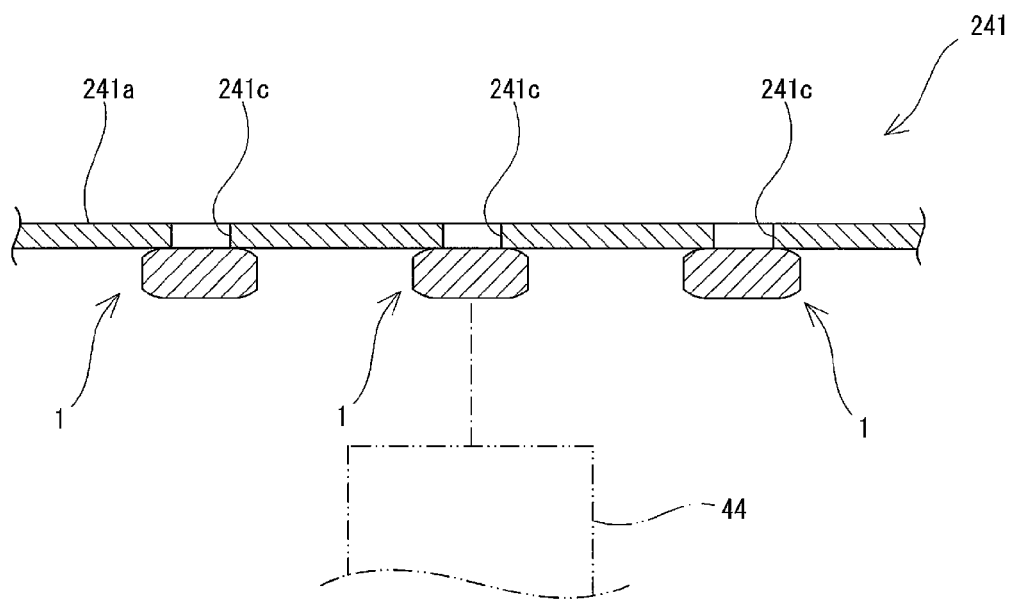
FIG. 13 is a cross-sectional view of the printer according to the embodiment, taken along line XIII-XIII in FIG. 12.

According to the configuration illustrated in FIG. 12 and FIG. 13, one suction hole 241c can suction one tablet 1. By this suction, the tablet 1 blocks the suction hole 241c. For example, the tablet 1 blocks the suction hole 241c located at the lower part of the conveying belt 241 in the first conveying section 24. Therefore, it is possible to prevent ejected ink from being disturbed by air suctioned by the suction hole 241c, so that the lower printing device 44 can stably eject ink. It should be noted that this configuration can be employed in the second conveying section 25.

Further, at the printer according to the above-described embodiments, the conveying device 23 is configured to convey a tablet 1 along a linear conveyance direction X. However, the configuration of the printer according to the present invention is not limited to the above-described configuration. For example, as illustrated in FIG. 14, the conveying device 23 may be configured to convey a tablet 1 along a curved conveyance direction X.

Figure 14:
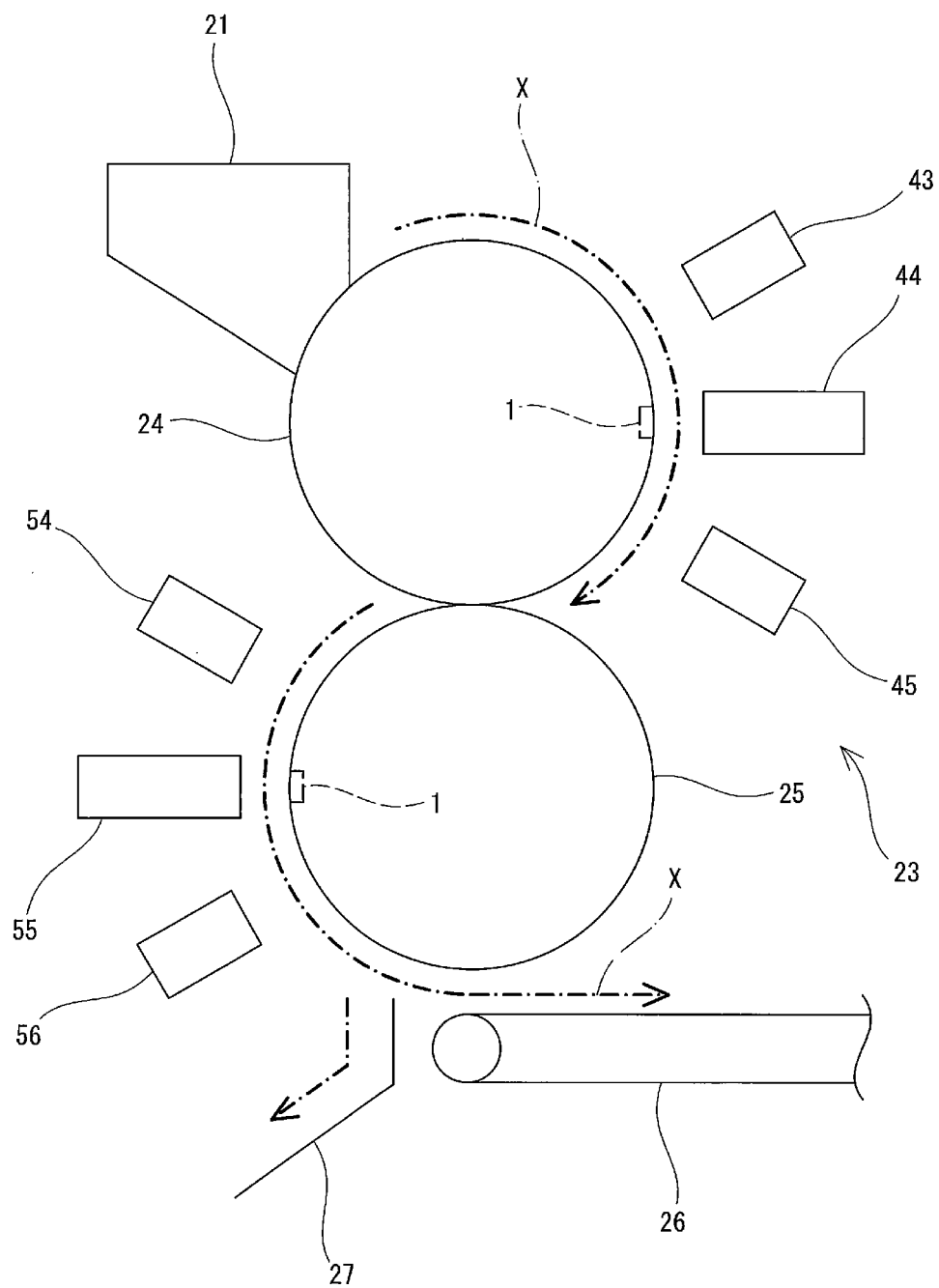
FIG. 14 is an overall front view of a printer according to yet another embodiment of the present invention.

The conveying device 23 of the printer illustrated in FIG. 14 includes a first conveying section 24 that rotates while holding by suction the tablet 1 received from the storage device 21 on its surface, and a second conveying section 25 that rotates while receiving the tablet 1 from the first conveying section 24 and holds by suction the tablet 1 on its surface. Further, the printer includes a discharging device 26 and a rejecting device 27 at the downstream side of the second conveying section 25.

The printer includes a first image pickup device 43, a first printing device 44 and a first printed portion image pickup device 45 outside the first conveying section 24. Further, the printer includes a second image pickup device 54, a second printing device 55 and a second printed portion image pickup device 56 outside the second conveying section 25.

Further, in the printer according to the above-described embodiments, the first conveying section 24 conveys the tablet 1 while contacting the upper side of the tablet 1, and the second conveying section 25 conveys the tablet 1 while contacting the lower side of the tablet 1. However, the printer according to the present invention is not limited to the above-described configuration.

For example, it is also possible to employ a configuration in which the second conveying section 25 conveys the tablet 1 while contacting a portion facing one lateral side of the tablet 1, and the first conveying section 24 conveys the tablet 1 while contacting a portion facing the other lateral side (the other side in a horizontal direction) of the tablet 1, and the first image pickup printing unit 4 picks up an image of the portion facing the one lateral side of the tablet 1 and performs printing on the portion of the one lateral side, and the second image pickup printing unit 5 picks up an image of the portion facing the other lateral side of the tablet 1 and performs printing on the portion of the other lateral side.

Further, the printer according to the above-described embodiments is configured so that after the lower dividing line judging section 622a (upper dividing line judging section 626a) performs judgment (judgment as to whether or not there is a dividing line), the lower checking section 623 (upper checking section 627) performs check (check of the shape, check of a foreign substance and check of a crack or chipped portion). However, the printer according to the present invention is not limited to the above-described configuration. Specifically, the printer may be configured so that judgment as to whether or not there is a dividing line is performed between any of the check of the shape, check of a foreign substance and check of a crack or chipped portion performed by the checking sections 623 and 627. For example, the printer may be configured so that check of the shape, check as to whether or not there is a dividing line, check of a foreign substance and check of a crack or chipped portion are performed in this order.

Further, in the printer according to the above-described embodiments, the printing devices 44 and 55 are non-contact type printing mechanisms (such as ink jet printers) which eject ink. However, the printer according to the present invention is not limited to the above-described configuration. For example, the printing devices 44 and 55 may be non-contact type printing mechanisms (such as laser markers) which perform impressing and printing on the tablet 1 by radiating laser. Further, the printing devices 44 and 45 may be contact type printing mechanisms (such as stamps) which perform printing by contacting the tablet 1.

Further, in the printer according to the above-described embodiments, an object on which printing is to be performed is a tablet 1. However, the printer according to the present invention is not limited to the above-described configuration.

For example, an object on which printing is to be performed may be a solid such as a candy.

Further, in the printer according to the above-described embodiments, what is printed on the tablet 1 is letters or characters. However, the printer according to the present invention is not limited to the above-described configuration. For example, what is printed on the tablet 1 may be patterns, designs, or the like. It should be noted that, hereinafter, these letters, characters, patterns, designs, or the like, may be simply referred to as a "symbol".

Further, the printer according to the above-described embodiments is configured such that the printing devices 44 and 55 and printing control sections 622 and 626 do not perform printing on the face having a dividing line 11 out of the face facing the one side (lower side in the above-described embodiments) and the face facing the other side (upper side in the above-described embodiments) of the tablet 1. However, the printer according to the present invention is not limited to the above-described configuration. For example, the printing devices 44 and 55 and the printing control sections 622 and 626 may be configured to perform printing also on the face having the dividing line 11 of the tablet 1. Six specific examples of the printer having such a configuration will be described below.

First, a first specific example of the printer performing printing also on the face having the dividing line 11 will be described below with reference to FIG. 15 to FIG. 20.

Figure 15:
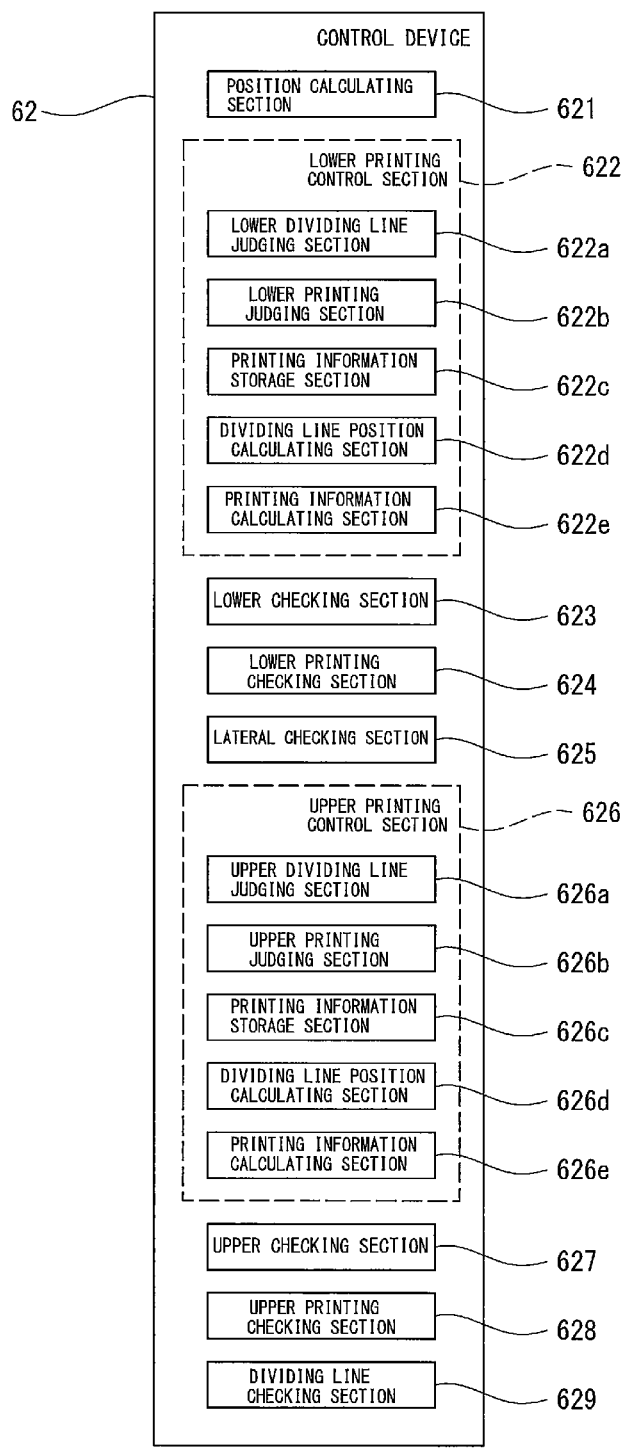
FIG. 15 is a block diagram of a printer according to yet another embodiment of the present invention.

In the control device 62 of this printer, as illustrated in FIG. 15, the lower printing control section 622 includes a lower dividing line judging section 622a, a lower printing judging section 622b and a printing information storage section 622c. Further, the lower printing control section 622 includes a dividing line position calculating section 622d that calculates the position of the dividing line 11 based on the image picked up by the lower image pickup device 43 and a printing information calculating section 622e that calculates information to be printed by the lower printing device 44 based on the calculation result of the dividing line position calculating section 622d.

Further, the upper printing control section 626 includes an upper dividing line judging section 626a, an upper printing judging section 626b and a printing information storage section 626c. Further, the upper printing control section 626 includes a dividing line position calculating section 626d that calculates the position of the dividing line 11 based on the image picked up by the upper image pickup device 54 and a printing information calculating section 626e that calculates information to be printed by the upper printing device 55 based on the calculation result of the dividing line position calculating section 626d.

Figure 16:
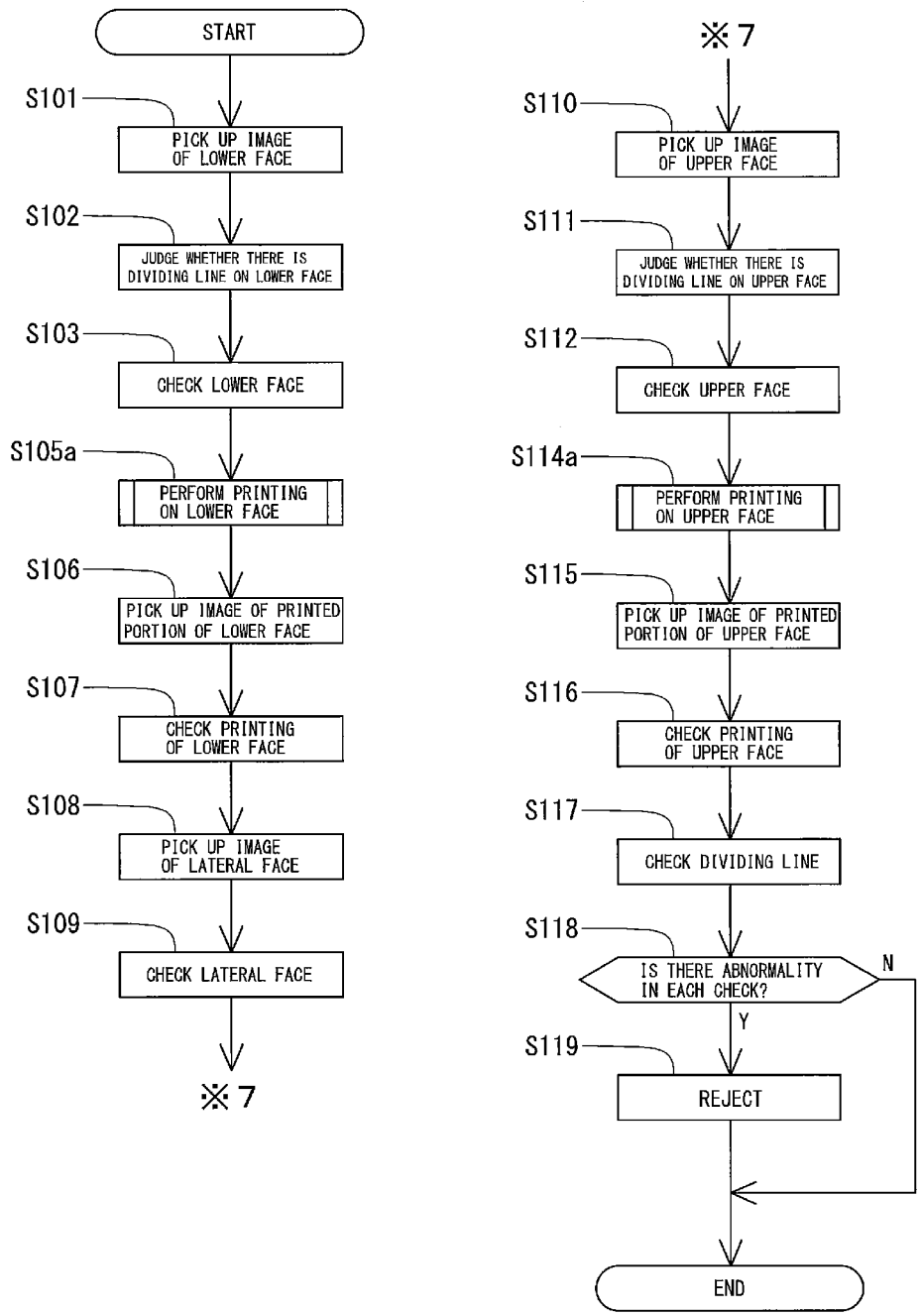
FIG. 16 is a flowchart of the printer according to the embodiment.
Figure 17:
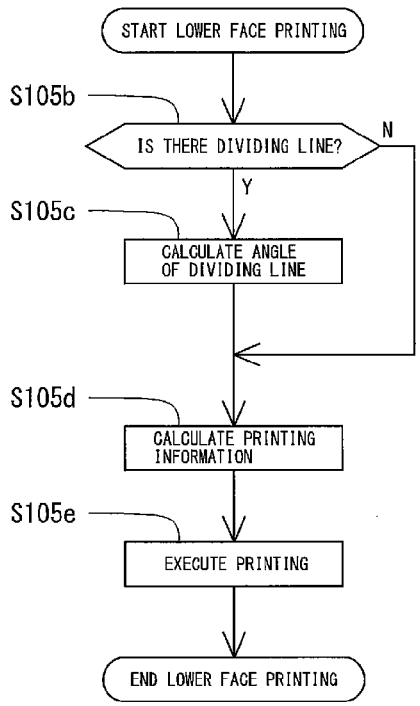
FIG. 17 is a flowchart of the printer according to the embodiment.
Figure 18:
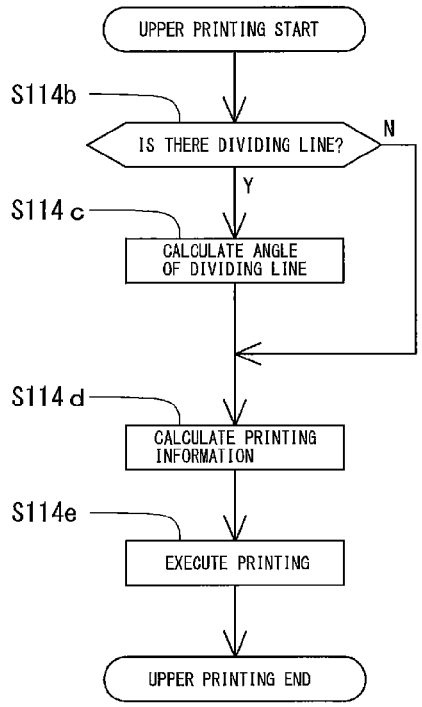
FIG. 18 is a flowchart of the printer according to the embodiment.

As illustrated in FIG. 16 to FIG. 18, a method for manufacturing a tablet 1 using this printer is different from the method for manufacturing a tablet 1 using the printer according to the above-described embodiments in a method in which printing is performed on the lower face of the tablet 1 (step 105a), and a method in which printing is performed on the upper face of the tablet 1 (step 114a). It should be noted because that steps 101 to 103, 106 to 112 and 115 to 119 are substantially the same as those according to the above-described embodiments, the explanation thereof will be omitted.

In this printer, after the lower checking section 623 checks whether the lower face of the tablet 1 is normal or abnormal (step 103), the lower printing device 44 performs printing on the lower face of the tablet 1 (step 105a). This printing (step 105a) is performed as described below.

First, the lower dividing line judging section 622a judges whether or not there is a dividing line 11 based on the image picked up by the lower image pickup device 43 (step 105b). When there is no dividing line 11 on the lower face of the tablet 1 (step 105b: "N"), the printing information calculating section 622e retrieves printing information stored in the printing information storage section 622c (step 105d), and the lower printing device 44 prints the information retrieved by the printing information calculating section 622e on the lower face of the tablet 1.

Conversely, when there is a dividing line 11 on the lower face of the tablet 1 (step 105b: "Y"), the dividing line position calculating section 622d calculates an angle by which the dividing line 11 rotates with respect to a predetermined position based on the image picked up by the lower image pickup device 43 (step 105c). Subsequently, the printing information calculating section 622e retrieves printing information stored in the printing information storage section 622c and calculates the retrieved printing information so as to rotate by the angle calculated by the dividing line position calculating section 622d (step 105d). The lower printing device 44 performs printing on the lower face of the tablet 1 based on the information calculated by the printing information calculating section 622e.

Further, in this printer, after the upper checking section 627 checks whether the upper face of the tablet 1 is normal or abnormal (step 112), the upper printing device 55 performs printing on the upper face of the tablet 1 (step 114a). This printing (step 114a) will be described below.

First, the upper dividing line judging section 626a judges whether or not there is a dividing line 11 based on the image picked up by the upper image pickup device 54 (step 114b). When there is no dividing line 11 on the upper face of the tablet 1 (step 114b: "N"), the printing information calculating section 622e retrieves the printing information stored in the printing information storage section 626c (step 114d). The upper printing device 55 prints the information retrieved by the printing information calculating section 626e on the upper face of the tablet 1.

Conversely, when there is a dividing line 11 on the upper face of the tablet 1 (step 114b: "Y"), the dividing line position calculating section 626d calculates an angle by which the dividing line 11 rotates with respect to a predetermined position based on the image picked up by the upper image pickup device 54 (step 114c). Subsequently, the printing information calculating section 626e retrieves the printing information stored in the printing information storage section 626c and calculates the retrieved information so as to rotate by the angle calculated by the dividing line position calculating section 626d (step 114d). The upper printing device 55 performs printing on the upper face of the tablet 1 based on the information calculated by the printing information calculating section 626e.

Figure 19:
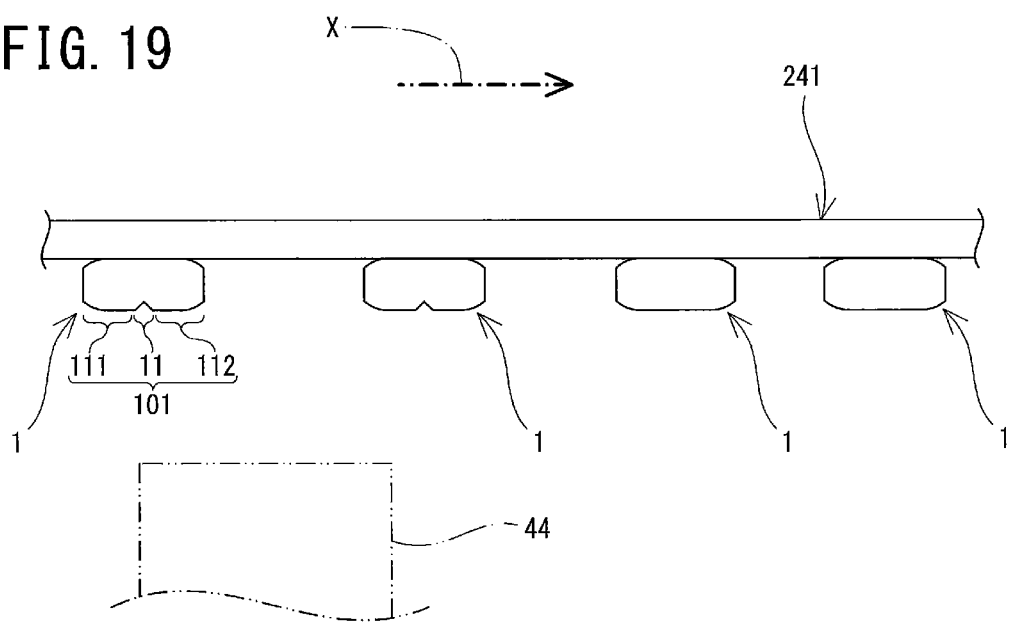
FIG. 19 is a partial enlarged front view of a first conveying section of the printer according to the embodiment.
Figure 20:
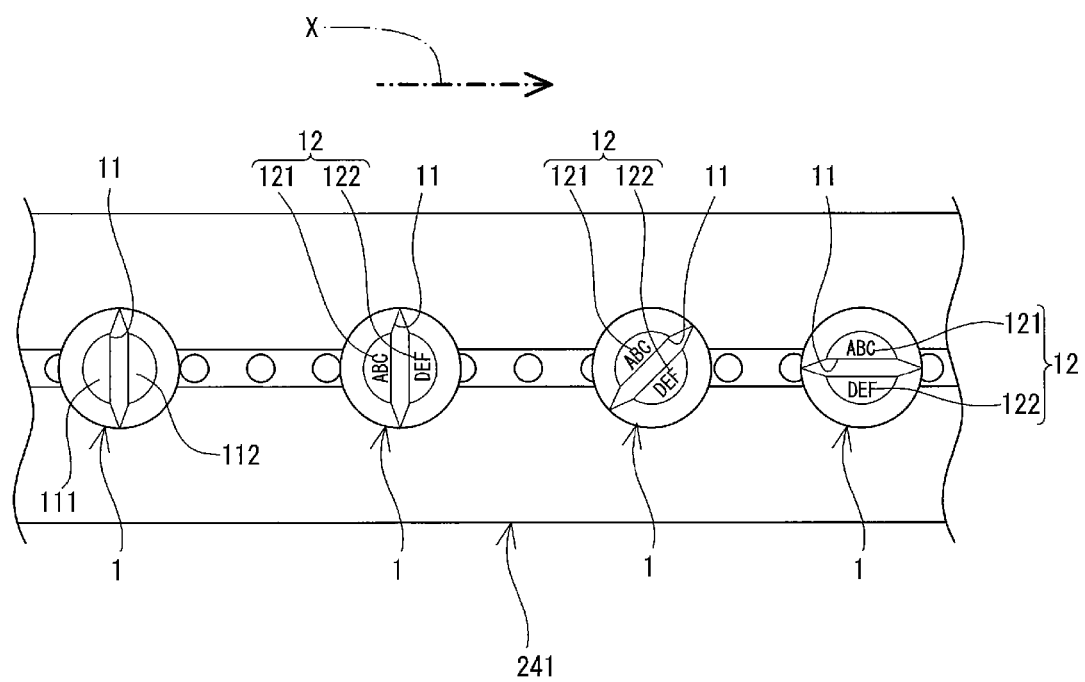
FIG. 20 is a partial enlarged bottom view of the first conveying section of the printer according to the embodiment.

According to the above-described configuration, even when the tablets 1 are conveyed by the conveying belt 241 in a state where the dividing lines 11 are positioned at various positions, as illustrated in FIG. 19 and FIG. 20, the lower printing device 44 can perform printing in the same way using the dividing line 11 as a reference. Therefore, for example, the printed portion (symbol) 12 may be a character printed along the dividing line 11 of the tablet 1. Specifically, the lower printing device 44 may print a first symbol 121 in a region 111 at one side with respect to the dividing line 11 while printing a second symbol 122 in a region 112 at the other side, on the face 101 where the dividing line 11 is provided at the tablet 1.

Next, a second specific example of the printer performing printing also on the face having a dividing line 11 will be described below with reference to FIG. 21 to FIG. 23.

Figure 21:
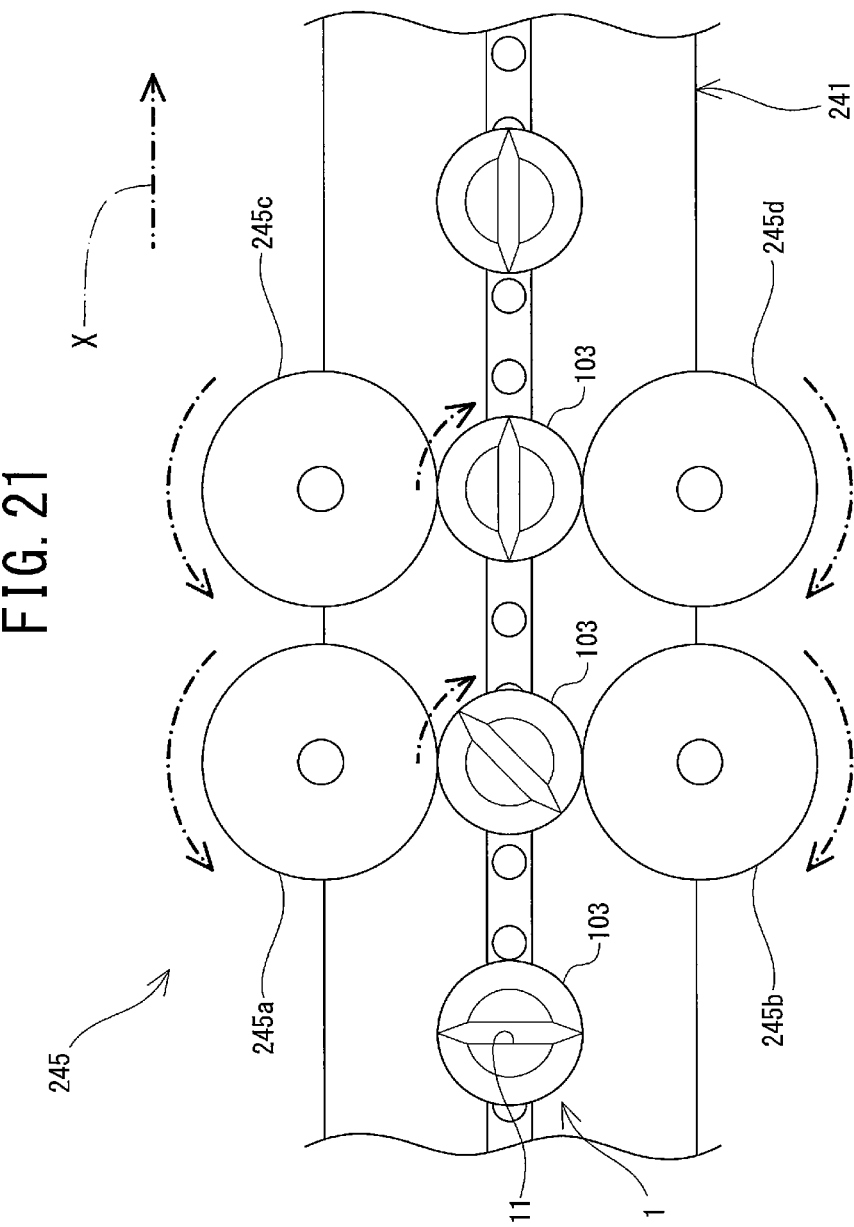
FIG. 21 is a partial enlarged bottom view of a first conveying section of a printer according to yet another embodiment of the present invention.
Figure 22:
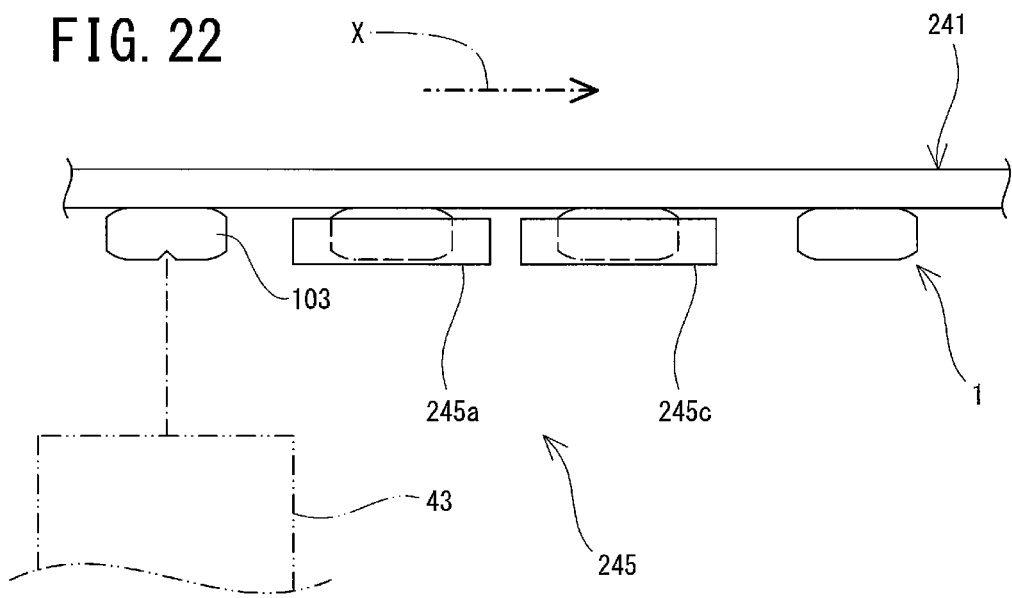
FIG. 22 is a partial enlarged front view of a first conveying section of the printer according to the embodiment.
Figure 23:
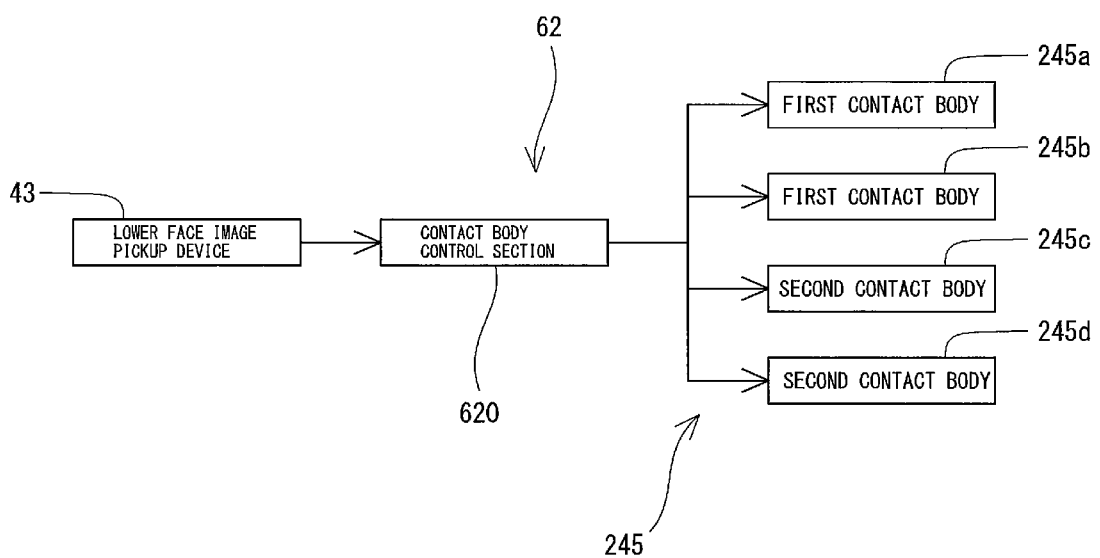
FIG. 23 is a block diagram of the printer according to the embodiment.

In this printer, as illustrated in FIG. 21 to FIG. 23, the first conveying section 24 includes a dividing line position aligning device 245 that aligns the positions of the dividing lines 11 (that is, directions of the groove-shaped dividing lines extending straight) between the lower image pickup device 43 and the lower printing device 44. The dividing line position aligning device 245 includes a pair of first contact bodies 245a and 245b that are disposed at the both sides of the tablet 1, and a pair of second contact bodies 245c and 245d that are disposed at the both sides of the tablet 1. Further, the control device 62 includes a contact body control section 620 that controls each of the contact bodies 245a to 245d.

It should be noted that, in this specific example, the dividing line position aligning device 245 configures a dividing line direction aligning section.

The first contact bodies 245a and 245b are disposed at the downstream side of the lower image pickup device 43 and below the first conveying belt 241. Further, the first contact bodies 245a and 245b are formed in a circular shape when seen from the bottom (as illustrated in FIG. 21) and are disposed distant from each other by a predetermined distance so that the peripheries thereof contact the periphery of the tablet 1 (cylindrical periphery 103). The first contact bodies 245a and 245b rotate at different speeds to thereby rotate (specifically, rotate around a central axis of the periphery 103) the tablet 1 which the first contact bodies 245a and 245b contact at the same time.

The second contact bodies 245c and 245d are disposed at the downstream side of the first contact bodies 245a and 245b and below the first conveying belt 241. Further, the second contact bodies 245c and 245d are formed in a circular shape when seen from the bottom (as illustrated in FIG. 21) and are disposed distant from each other by a predetermined distance so that the peripheries thereof contact the periphery of the tablet 1 (periphery 103). The second contact bodies 245c and 245d rotate at different speeds to thereby rotate the tablet 1 which the second contact bodies 245c and 245d contact at the same time.

The contact body control section 620 calculates an angle by which the dividing line 11 rotates with respect to the predetermined position based on the image picked up by the lower image pickup device 43, and, further, calculates a rotation speed of each of the contact bodies 245a to 245d based on the calculated angle. The contact body control section 620 controls the contact bodies 245a to 245d to rotate at the calculated rotation speed when the contact bodies 245a to 245d contact the tablet 1.

According to the above-described configuration, even when the tablet 1 is conveyed by the conveying belt 241 in a state where the dividing line 11 is positioned at various positions, the dividing line position aligning device 245 can position the dividing line 11 at a predetermined position by rotating the tablet 1. Whereby, the lower printing device 44 can perform printing on the tablet 1 in the same way using the dividing line 11 as a reference.

It should be noted that the second conveying section 25 may also include a dividing line position aligning device that is provided between the upper image pickup device 54 and the upper printing device 55 and that aligns the positions of the dividing lines 11. Further, the number of pairs of the contact bodies 245a and 245b (245c and 245d) is not limited to two, and the printer may be configured to include one, or three or more pairs.

Next, a third specific example of the printer performing printing also on the face having a dividing line 11 will be described below with reference to FIG. 24 to FIG. 26.

Figure 24:
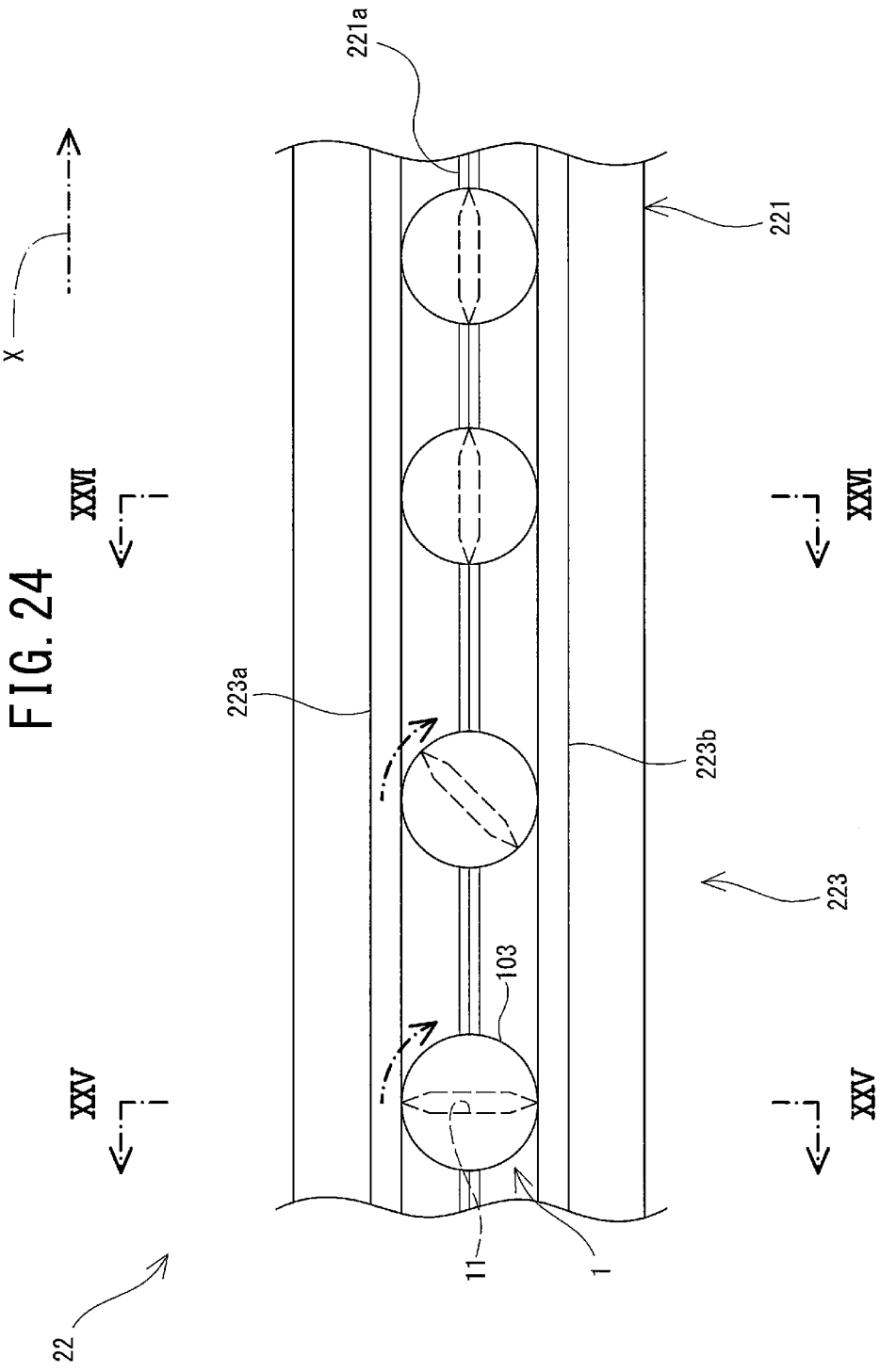
FIG. 24 is a partial enlarged plane view of a first conveying section of a printer according to yet another embodiment of the present invention.
Figure 25:
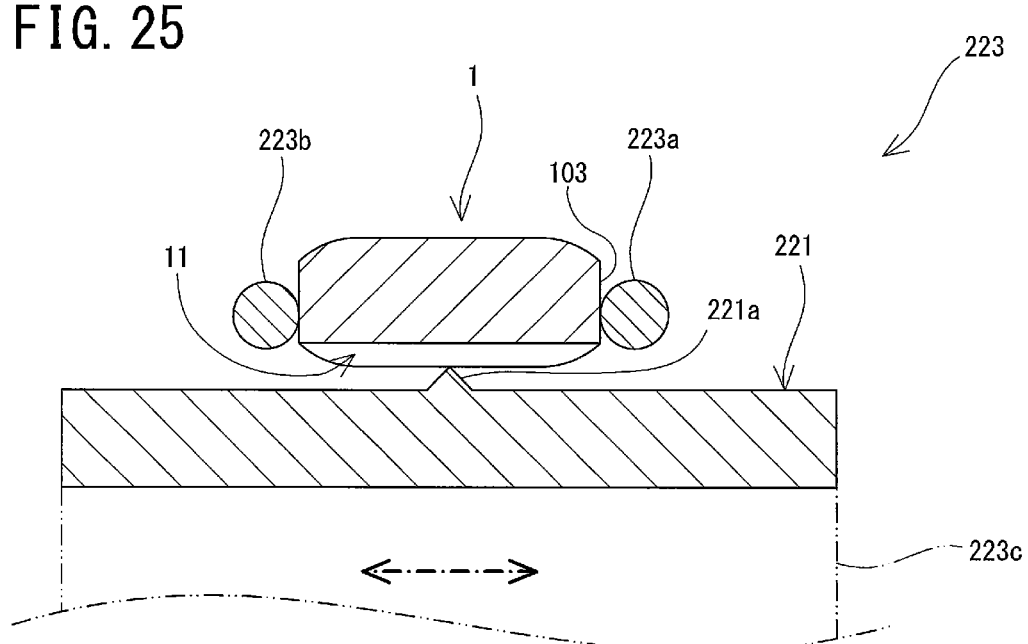
FIG. 25 is an enlarged cross-sectional view of the printer according to the embodiment, taken along line XXV-XXV in FIG. 24.
Figure 26:
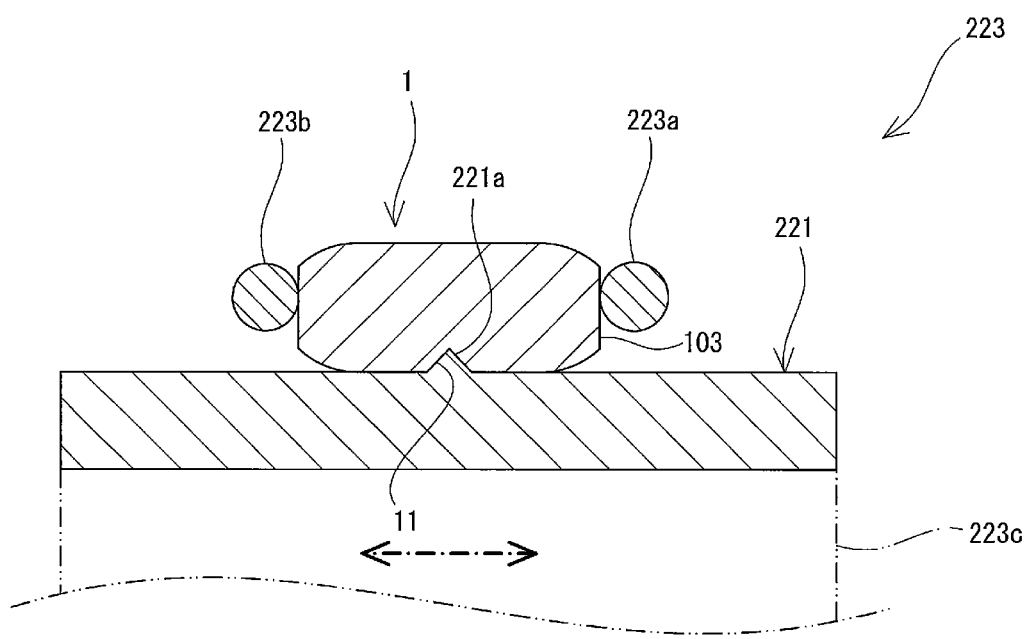
FIG. 26 is an enlarged cross-sectional view of the printer according to the embodiment, taken along line XXVI-XXVI in FIG. 24.

In this printer, as illustrated in FIG. 24 to FIG. 26, the carrying device 22 includes a dividing line position aligning device 223 that aligns the positions of the dividing lines 11 of the tablets 1 aligned by the aligning section 222. The dividing line position aligning device 223 includes a pair of guide sections 223a and 223b that are disposed distant from each other so as to hold a tablet 1 therebetween, and a vibrating device 223c that vibrates the carrying belt 221. Further, the carrying belt 221 includes a protruding portion (protrusion) 221a which protrudes toward a central portion of a width direction and extends in a longitudinal direction (conveyance direction of the tablet 1) so at to be inserted (fitted) into the dividing line 11 of the tablet 1.

It should be noted that, in this specific example, the dividing line position aligning device 245 and the protruding portion 221a configure the dividing line direction aligning section that aligns the directions of the dividing lines 11 of the tablets 1 in a predetermined direction. The dividing line position aligning device 245 and the protruding portion 221a cooperate with each other to align the directions of the dividing lines 11 of the tablets 1 in a predetermined direction (in this specific example, in a direction the protruding portion 221a extends).

According to the above-described configuration, because the vibrating device 223c vibrates the carrying belt 221, the tablet 1 while being conveyed by the carrying belt 221 oscillates between the pair of guide sections 223a and 223b. Whereby, the tablet 1 which is placed on the protruding portion 221a in a state where the face on which the dividing line 11 is provided contacts the protruding portion 221a and the direction of the dividing line 11 is different from the direction of the protruding portion 221a, rotates around the central axis of the periphery 103. In this way, in the present embodiment, the pair of guide sections 223a and 223b contacting the tablet 1 and the vibrating device 223c that vibrates the carrying belt 221 on which the protruding portion 221a is provided cooperate with each other, so that the tablet 1 can rotate around the central axis on the protruding portion 221. That is, the pair of guide sections 223a and 223b, and the vibrating device 223c that vibrates the carrying belt 221 of the present embodiments are encompassed in the scope defined by the term the contact body in the appended claims.

Subsequently, when the direction in which the protruding portion 221a extends becomes the same as the direction in which the dividing line 11 extends, the protruding portion 221a is fitted into the dividing line 11 by the weight, or the like, of the tablet 1 itself. Specifically, when the dividing line 11 of the tablet 1 moves from the position where the dividing line 11 intersects with the protruding portion 221a of the carrying belt 221 as illustrated in FIG. 25 to the position where the dividing line 11 is parallel with the protruding portion 221a of the carrying belt 221, the protruding portion 221a is inserted in the dividing line 11. Whereby, because the protruding portion 221a comes into locking engagement with the dividing line 11, it is possible to prevent the tablet 1 positioned at a reference position from rotating.

Therefore, even when the tablet 1 is conveyed by the carrying belt 221 in a state where the dividing line 11 is positioned at various positions or extend in various directions, the dividing line position aligning device 223 oscillates the tablet 1, thereby positioning the dividing line 11 at a predetermined position (specifically, a position parallel with the protruding portion 221a). Whereby, the lower printing device 44 can perform printing on the tablets 1 in the same way using the dividing line 11 as a reference. It should be noted that when the tablet 1 is conveyed by the carrying device 22 with the dividing line 11 facing upward, the lower dividing line judging section 622a judges that there is "no dividing line" for the tablet 1, and the tablet 1 is returned to the storage device 21 or the upstream side of the carrying device 22.

Next, a fourth specific example of the printer performing printing also on the face having the dividing line 11 will be described below with reference to FIG. 27 to FIG. 29.

Figure 27:
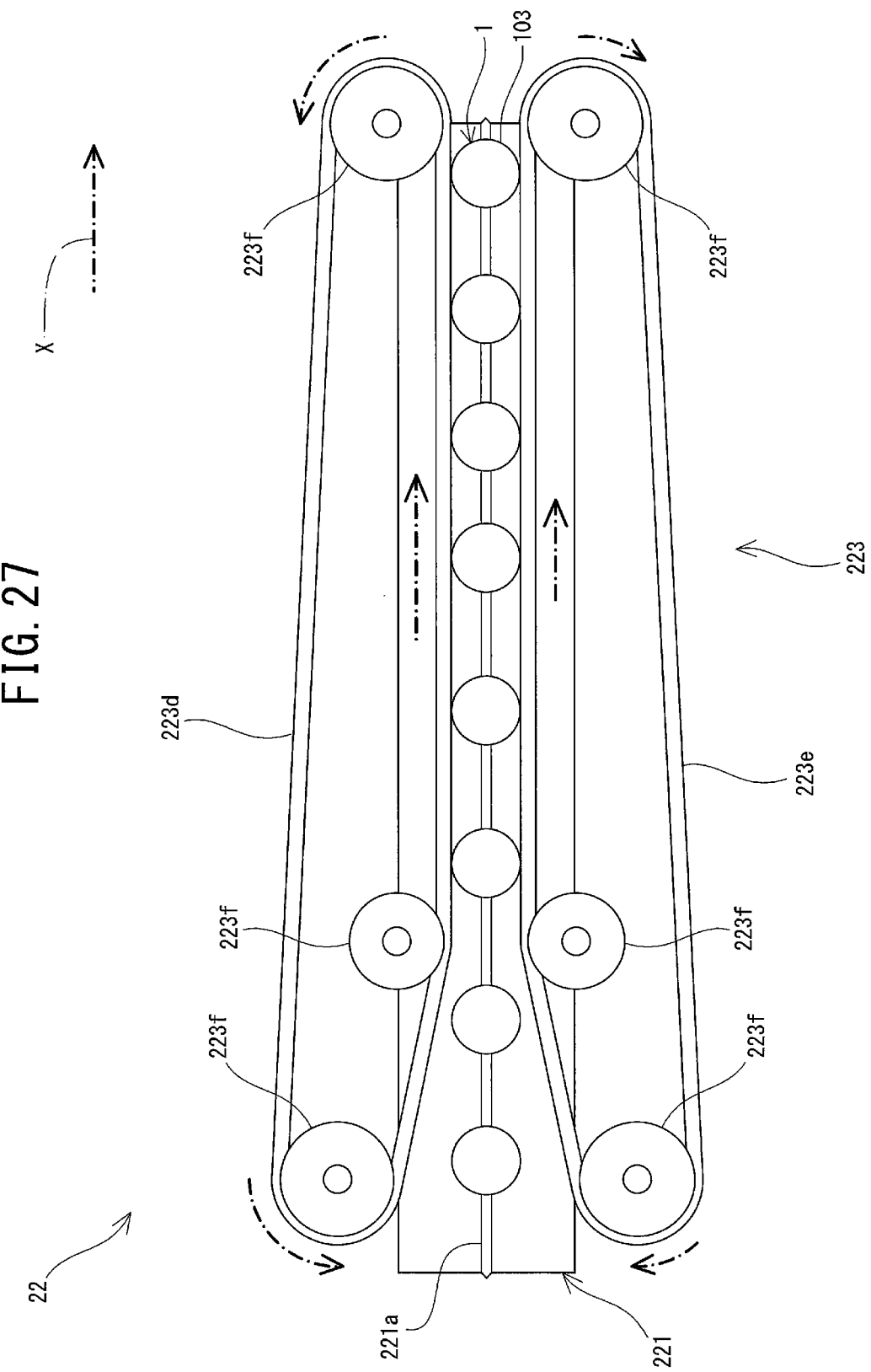
FIG. 27 is a plane view of a first conveying section of a printer according to yet another embodiment of the present invention.
Figure 28:
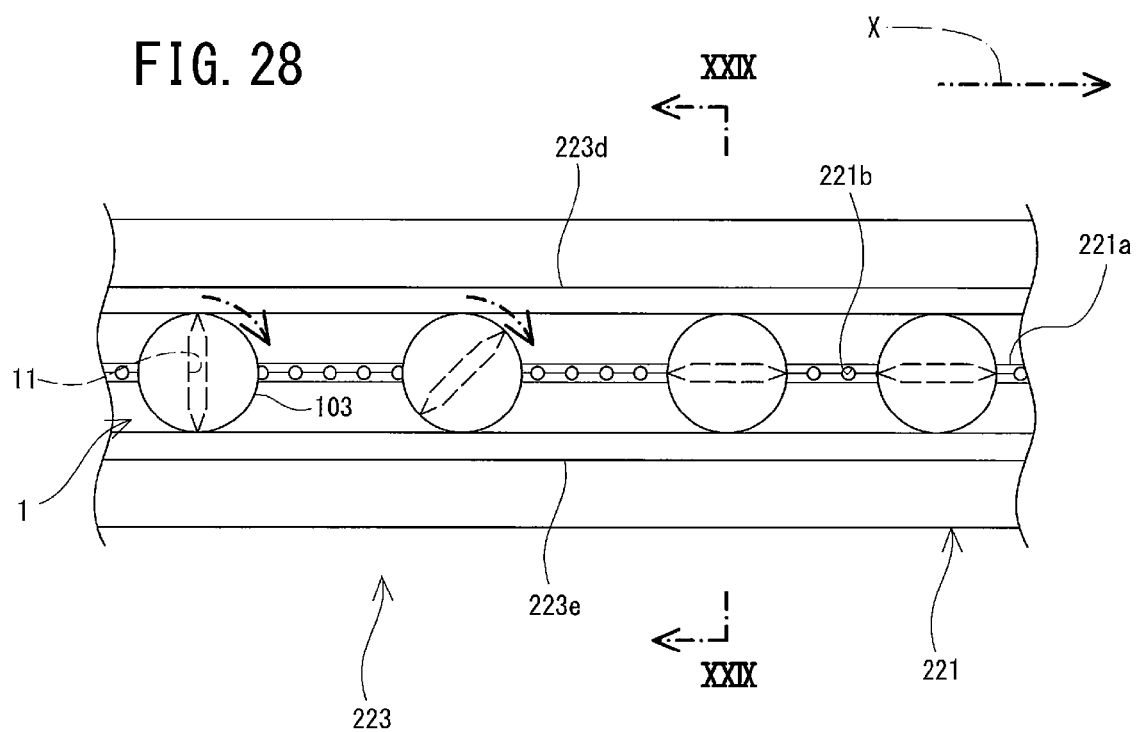
FIG. 28 is a partial enlarged plane view of the first conveying section of the printer according to the embodiment.
Figure 29:
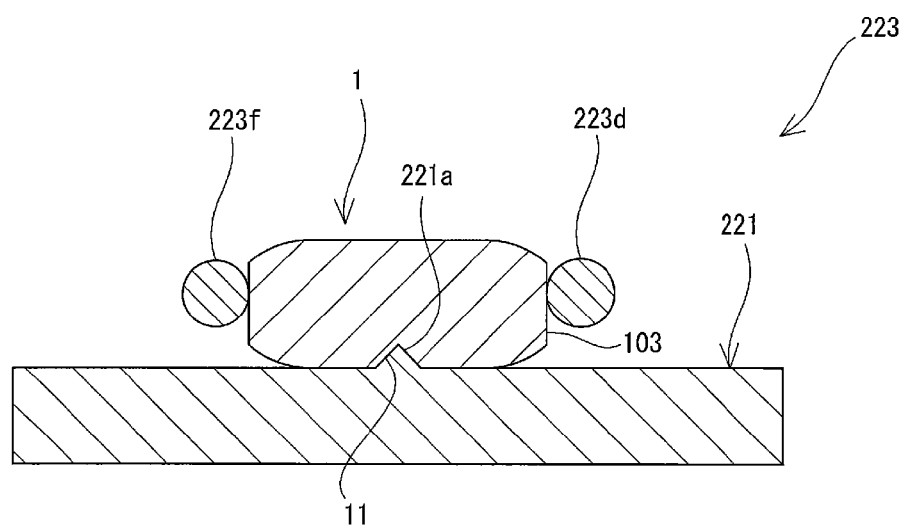
FIG. 29 is an enlarged cross-sectional view of the printer according to the embodiment, taken along line XXIX-XXIX in FIG. 28.

In this printer, as illustrated in FIG. 27 to FIG. 29, the carrying device 22 includes a dividing line position aligning device 223 that aligns the positions of the dividing lines 11 of the tablets 1 aligned by the aligning section 222. The dividing line position aligning device 223 includes a pair of contact bodies 223d and 223e that are disposed at the both sides of the tablet 1, and a plurality of rotators 223f between which the contact bodies 223d and 223e are hung. Further, the carrying belt 221 includes a protruding portion 221a that protrudes toward the central portion of a width direction and extends in the longitudinal direction so as to be inserted into the dividing line 11 of the tablet 1 and a plurality of suction holes 221b for suctioning the tablets 1 at the position of the protruding portion 221a.

It should be noted that, also in this specific example, the dividing line position aligning device 223 and the protruding portion 221a configure the dividing line direction aligning section. These dividing line position aligning device 223 and the protruding portion 221a cooperate with each other to align the directions of the dividing lines 11 of the tablets 1 in a predetermined direction. This will be described in detail below.

The contact bodies 223d and 223e are disposed at the downstream side of the aligning section 222 and above the carrying belt 221. The contact bodies 223d and 223e have portions along the conveyance direction X at the lateral sides and rotate endlessly. Specifically, the contact bodies 223d and 223e run in the same direction as the carrying belt 221. Further, the contact bodies 223d and 223e are disposed such that the lateral portions of the contact bodies 223d and 223e are parallel with each other and distant from each other, so that the lateral portions can contact the outer periphery (periphery 103) of the tablet 1. The contact bodies 223d and 223e run at different speeds, thereby rotating the tablet 1 which the contact bodies 223d and 223e contact. That is, the tablet 1 which is placed on the protruding portion 221a in a state where the face 101 on which the dividing line 11 is provided contacts the protruding portion 221a and the direction of the dividing line 11 is different from the direction of the protruding portion 221a, rotates around the central axis of the periphery 103.

According to the above-described configuration, because the contact bodies 223d and 223e contact the outer periphery (periphery 103) of the tablet 1 at their lateral portions, the tablet 1 while being conveyed by the carrying belt 221 rotates between the pair of contact bodies 223d and 223e. That is, the tablet 1 which is placed on the protruding portion 221a in a state where the face on which the dividing line 11 is provided contacts the protruding portion 221a and the direction of the dividing line 11 is different from the direction of the protruding portion 221a, rotates around the central axis of the periphery 103. As illustrated in FIG. 29, when the dividing line 11 of the tablet 1 becomes parallel with the protruding portion 221a of the carrying belt 221, the protruding portion 221a is inserted into the dividing line 11. Whereby, because the protruding portion 221a comes in to locking engagement with the dividing line 11, it is possible to prevent the tablet 1 positioned at the reference position from rotating.

It should be noted that when the dividing line 11 of the tablet 1 is not inserted into the protruding portion 221a, the suction hole 221b is not blocked. In this case, because a force for suctioning the tablet 1 is small, the tablet 1 rotates by a friction force between the pair of contact bodies 223d and 223e. Conversely, when the dividing line 11 of the tablet 1 is inserted into the protruding portion 221a, the suction hole 221b is blocked. In this case, because a force for suctioning the tablet 1 becomes great, in cooperation with a force of the protruding portion 221a coming into locking engagement with the dividing line 11, it is possible to prevent rotation of the tablet 1 positioned at the reference position more reliably.

Therefore, even when the tablet 1 is conveyed by the carrying belt 221 in a state where the dividing line 11 is positioned at various positions, the dividing line position aligning device 223 can set the dividing line 11 at a predetermined position (specifically, position parallel with the protruding portion 221a) by rotating the tablet 1. Whereby, the lower printing device 44 can perform printing on the tablets 1 in the same way using the dividing line 11 as a reference. It should be noted that when the tablet 1 is conveyed by the carrying device 22 with the dividing line 11 facing upward, the lower dividing line judging section 622a judges that "there is no dividing line" for the tablet 1, and the tablet 1 is returned to the storage device 21 or the upstream side of the carrying device 22.

Next, a fifth specific example of the printer performing printing also on the side having the dividing line 11 will be described below with reference to FIG. 30 and FIG. 31.

Figure 30:
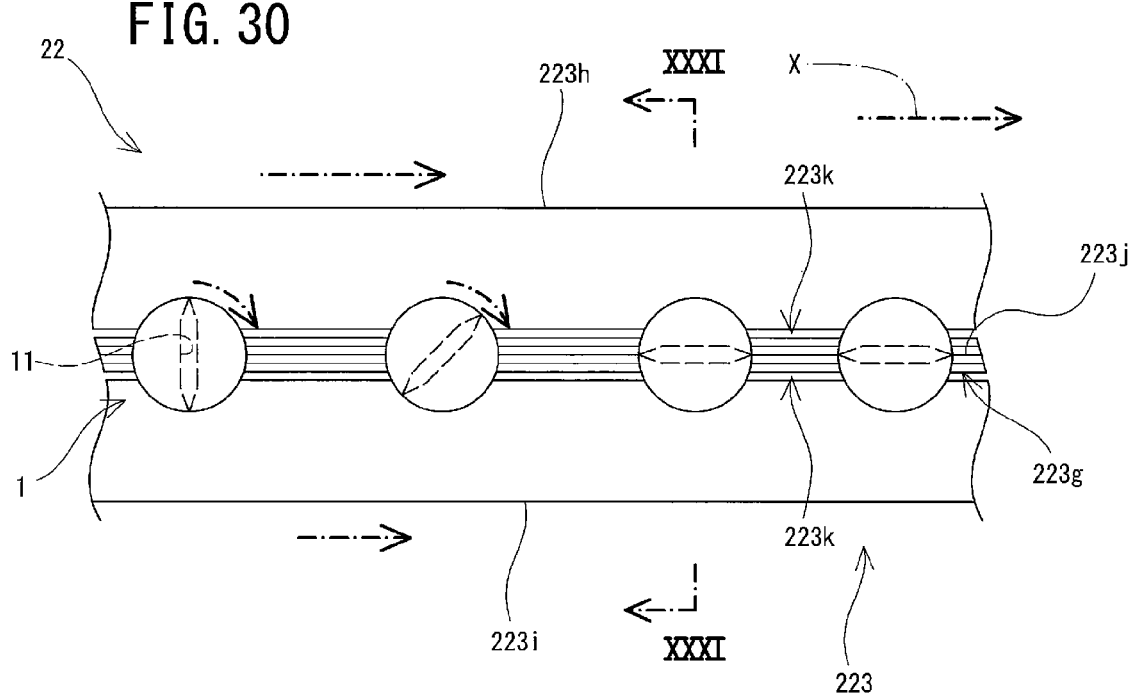
FIG. 30 is a partial enlarged plane view of a first conveying section of a printer according to yet another embodiment of the present invention.
Figure 31:
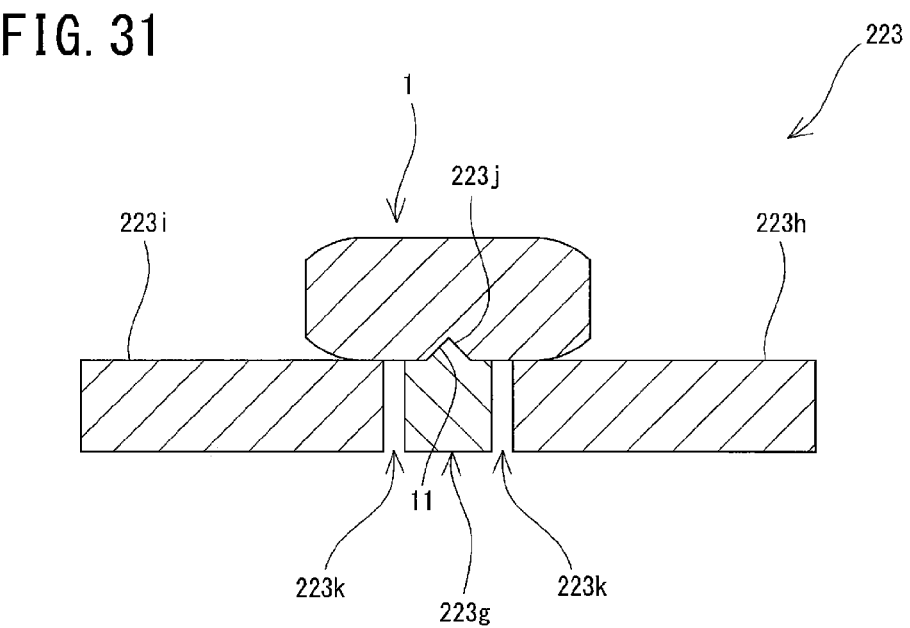
FIG. 31 is an enlarged cross-sectional view of the printer according to the embodiment, taken along line XXXI-XXXI in FIG. 30.

In this printer, as illustrated in FIG. 30 and FIG. 31, the carrying device 22 includes a dividing line position aligning device 223 that aligns the positions of the dividing lines 11 of the tablets 1 aligned by the aligning section 222. The dividing line position aligning device 223 includes a placement part 223g that is disposed along the conveyance direction X so that the tablet 1 is to be placed thereon, a first carrying belt 223h that is disposed at one lateral side of the placement part 223g, has a portion along the conveyance direction X at the upper part and rotates endlessly, and a second carrying belt 223i that is disposed at the other lateral side of the placement part 223g, has a portion along the conveyance direction X at the upper part and rotates endlessly. It should be noted that, in this specific example, the dividing line position aligning device 223 configures the dividing line direction aligning section.

The placement part 223g includes a protruding portion 223j that protrudes toward the central portion of the width direction and extends in the longitudinal direction so as to be inserted into the dividing line 11 of the tablet 1. Suctioning sections 223k for suctioning the tablet 1 are provided between the placement part 223g and the carrying belts 223h and 223i. The pair of the carrying belts 223h and 223i run at different speeds.

According to the above-described configuration, because the upper part of the pair of carrying belts 223h and 223i running at different speeds contact the lower face of the tablet 1, the tablet 1 suctioned by the suctioning section 223k rotates on the placement part 223g. The tablet 1 rotates around the central axis of the periphery, the tablet 1 being placed on the protruding portion 223j, and, as illustrated in FIG. 31, the dividing line 11 of the tablet 1 becomes parallel with the protruding portion 223j of the placement part 223g. At this time, the protruding portion 223j is inserted into the dividing line 11. Whereby, because the protruding portion 223j comes into locking engagement with the dividing line 11, it is possible to prevent the tablet 1 positioned at the reference position from rotating.

Therefore, even when the tablet 1 is conveyed in a state where the dividing line 11 is positioned at various positions, the dividing line position aligning device 223 can position the dividing line 11 in a predetermined position (specifically, position parallel with the protruding portion 223*j*) by rotating the tablet 1. Whereby, the lower printing device 44 can perform printing on the tablets 1 in the same way using the dividing line 11 as a reference. It should be noted that when the tablet 1 is conveyed by the carrying device 22 with the dividing line 11 facing upward, the lower dividing line judging section 622*a* judges that "there is no dividing line" for the tablet 1, and the tablet 1 is returned to the storage device 21 or the upstream side of the carrying device 22.

Figure 32:
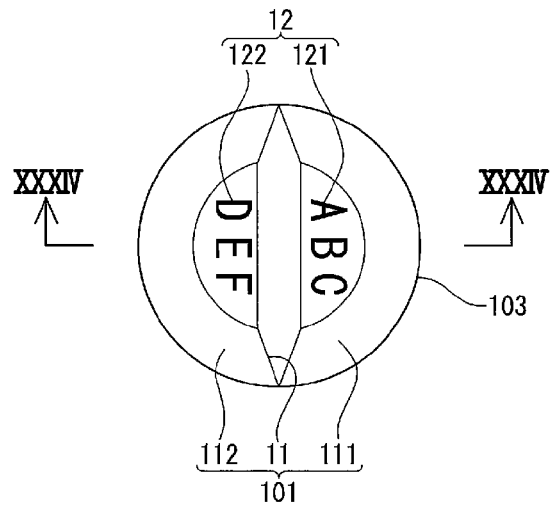
FIG. 32 is a plane view of a tablet on which printing is performed by a printer according to yet another embodiment of the present invention.
Figure 33:
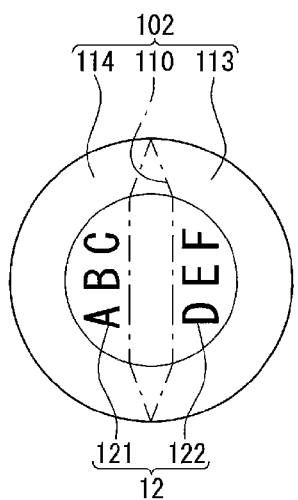
FIG. 33 is a bottom view of the tablet on which printing is performed by the printer according to the embodiment.
Figure 34:
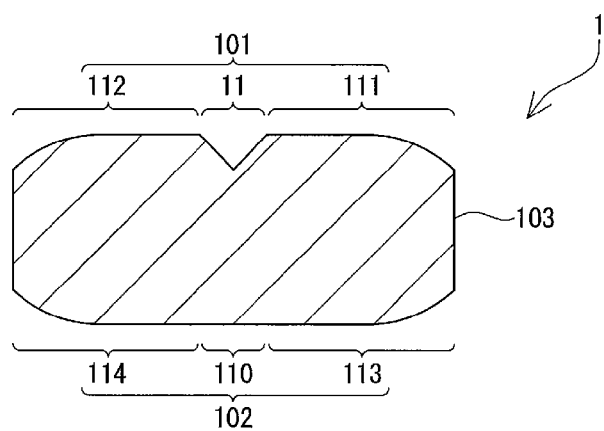
FIG. 34 is an enlarged cross-sectional view of the tablet on which printing is performed by the printer according to the embodiment, taken along line XXXIV-XXXIV in FIG. 32.

Next, a sixth specific example of the printer performing printing also on the face having the dividing line 11 will be described below with reference to FIG. 32 to FIG. 34. It should be noted that as illustrated in FIG. 32 to FIG. 34, the surface of the tablet 1 of this specific example is comprised of a first face 101 which is a face facing one side (upper side in FIG. 34), a second face 102 which is a face facing the other side (lower side in FIG. 34) and a cylindrical periphery 103 which connects the circumference of the first face 101 and the circumference of the second face 102. Further, in the tablet 1 of this specific example, the dividing line 11 is provided on the first face 101.

In this printer, when the tablet 1 is conveyed by the first conveying section 24 while the first face 101 on which the dividing line 11 is provided faces downward, the lower printing device 45 and the upper printing device 55 respectively perform printing on the faces 101 and 102 of the tablet 1 as described below.

As illustrated in FIG. 32 and FIG. 34, the lower printing device 45 prints the first symbol 121 in the first region 111 on one side (left side in FIG. 32) with respect to the dividing line 11 and prints the second symbol 122 in the second region 112 on the other side (right side in FIG. 32) on the first face 101. This second symbol 122 is a symbol different from the first symbol 121. Further, as illustrated in FIG. 33 and FIG. 34, the upper printing device 55 prints the second symbol 122 in a third region 113 (that is, a region on one side (left side in FIG. 33) with respect to a portion 110 which corresponds to the dividing line 11 on the first face 101) which corresponds to the first region 111 and prints the first symbol 121 in a fourth region 114 (that is, a region on the other side (right side in FIG. 33) with respect to the portion 110 which corresponds to the dividing line 11 on the first face 101) which corresponds to the second region 112 on the second face 102.

Meanwhile, when the tablet 1 is conveyed by the first conveying section 24 while the second face 102 on which the dividing line 11 is not provided faces downward, the lower printing device 45 and the upper printing device 55 respectively perform printing on the faces 101 and 102 of the tablet 1 as described below.

The lower printing device 45 prints the first symbol 121 in the third region 113 and prints the second symbol 122 in the fourth region 114 on the second face 102. Further, the upper printing device 55 prints the second symbol 122 in the first region 111 and prints the first symbol 121 in the second region.

According to this configuration, on the tablet 1 on which printing is performed using this printer, the both symbols of the first symbol 121 and the second symbol 122 are printed at either piece when the tablet 1 is divided at the position of the dividing line 11.

While, in the printer of this specific example, symbols printed in the regions 111, 112, 113 and 114 are different depending on the direction of the tablet 1 being conveyed by the first conveying section 24, the present invention is not limited to this configuration. For example, the printer may be configured to print the first symbol 121 in the first region 111, print the second symbol 122 in the second region 112, print the second symbol 122 in the third region 113, and print the first symbol 121 in the fourth region 114 regardless of the direction of the tablet 1 being conveyed by the first conveying section 24.

Figure 35:
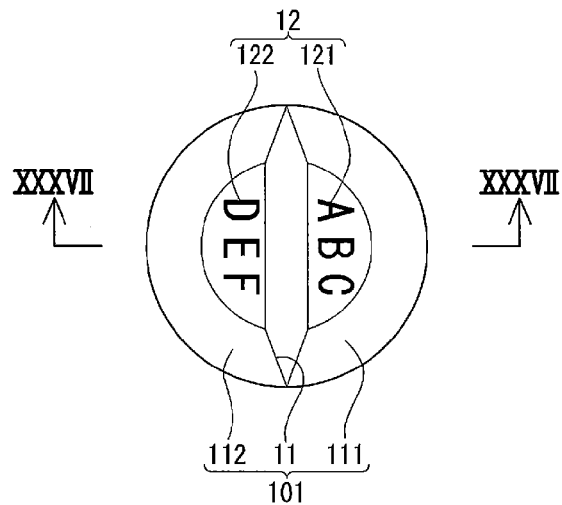
FIG. 35 is a plane view of a tablet according to another embodiment of the present invention.
Figure 36:
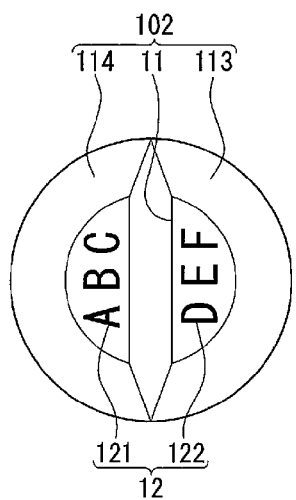
FIG. 36 is a bottom view of the tablet according to the embodiment.
Figure 37:
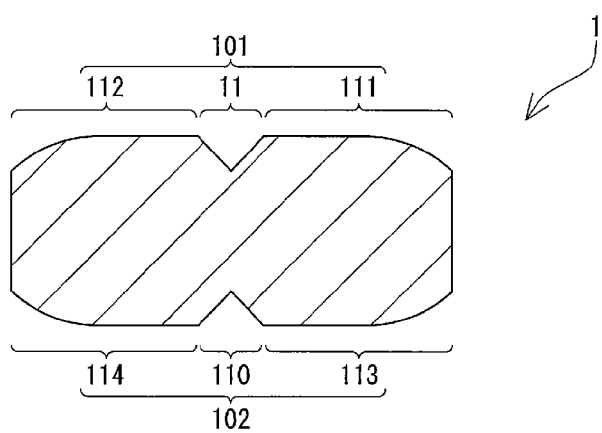
FIG. 37 is an enlarged cross-sectional view of the tablet according to the embodiment, taken along line XXXVII-XXXVII in FIG. 35.

It should be noted that while, in this specific example, the dividing line 11 is provided only on one face (the first face 101) of the tablet 1, the dividing lines 11 may be provided on the both faces (the first and the second faces 101 and 102), as illustrated in FIG. 35 to FIG. 37.

Further, while the printer in the above-described embodiments and the specific examples does not perform printing within the dividing line 11 or within the portion 110 which corresponds to the dividing line 11, the present invention is not limited to this configuration. For example, the printer may be configured to perform printing in at least one region of a region excluding the dividing line 11 on the face facing the one side (for example, the first region 111 and the second region 112 on the first face 101 in the sixth specific example), and a region excluding the portion 110 which corresponds to the dividing line 11 on the face facing the other side (for example, the third region 113 and the fourth region 114 on the second face 101 in the sixth specific example), and perform printing within the dividing line 11 and within the portion 110 which corresponds to the dividing line 11.

It should be noted that the printer and the tablet of the present invention are not limited to the above-described embodiments and the above-described specific examples, and, of course, can be modified in various ways without departing from the spirit of the present invention.

REFERENCE SIGNS LIST

1 . . . Tablet
2 . . . Conveying unit
3 . . . Housing
4 . . . First image pickup printing unit
5 . . . Second image pickup printing unit
6 . . . Control unit
11 . . . Dividing line
23 . . . Conveying device
43 . . . Lower image pickup device (first image pickup device)
44 . . . Lower printing device (first printing device)
54 . . . Upper image pickup device (second image pickup device)
55 . . . Upper printing device (second printing device)
62 . . . Control device
622*a* . . . Lower dividing line judging section (first dividing line judging section)
622*b* . . . Lower printing judging section (first printing judging section)
623 . . . Lower checking section (first checking section)
626*a* . . . Upper dividing line judging section (second dividing line judging section)
626*b* . . . Upper printing judging section (second printing judging section)
627 . . . Upper checking section (second checking section)
629 . . . Dividing line checking section

The invention claimed is:
1. A printer comprising:
a) a conveying device that conveys a tablet;

b) a first printing device capable of performing printing on a face facing one side in an orthogonal direction to a conveyance direction of the tablet while being conveyed;
c) a second printing device capable of performing printing on a face facing the other side in the orthogonal direction of the tablet while being conveyed;
d) wherein the tablet has a groove-shaped dividing line for dividing the tablet on at least one face out of the face facing the one side and the face facing the other side;
e) wherein the first printing device can perform printing in a region on the face facing the one side which region excluding the dividing line or a portion which corresponds to the dividing line provided on the face facing the other side;
f) wherein the second printing device can perform printing in a region on the face facing the other side which region excluding the dividing line or a portion which corresponds to the dividing line provided on the face facing the one side;
g) an aligning section that supplies a plurality of tablets to the conveying device in a state where the plurality of tablets are aligned in the conveyance direction,
h) wherein the conveying device comprises a dividing line direction aligning section that is disposed at an upstream side of the first printing device and the second printing device and that aligns a direction of the dividing line of each of the tablets in a predetermined direction; and
i) wherein the dividing line direction aligning section comprises:
  1) a protrusion that extends in the conveyance direction and that has a cross-sectional shape corresponding to a cross-sectional shape of the dividing line of the tablet; and
  2) a contact body that rotates the tablet around a predetermined axis facing in the orthogonal direction, the tablet being placed on the protrusion in a state where, out of the face facing the one side and the face facing the other side, a face on which the dividing line is provided contacts the protrusion and a direction of the dividing line is different from a direction of the protrusion.

2. The printer according to claim 1, further comprising:
a first image pickup device that picks up an image of the face facing the one side of each tablet while being conveyed; and
a second image pickup device that picks up an image of the face facing the other side of each tablet while being conveyed, wherein the dividing line direction aligning section rotates each tablet while being conveyed around a predetermined axis facing in the orthogonal direction so that the direction of the dividing line becomes the predetermined direction based on at least one of an image pickup result of the first image pickup device and an image pick up result of the second image pickup device.

3. The printer according to claim 2, wherein
the first printing device prints a first symbol in a first region on one side with respect to the dividing line or a portion which corresponds to the dividing line and prints a second symbol different from the first symbol in a second region on the other side on the face facing the one side of each tablet, and
the second printing device prints the second symbol in a region corresponding to the first region and prints the first symbol in a region corresponding to the second region on the face facing the other side of each tablet.

* * * * *